US011040942B1

(12) United States Patent
Pluth et al.

(10) Patent No.: US 11,040,942 B1
(45) Date of Patent: Jun. 22, 2021

(54) COMPOUND EMBODIMENTS FOR HYDROGEN SULFIDE PRODUCTION AND METHODS OF MAKING AND USING THE SAME

(71) Applicant: University of Oregon, Eugene, OR (US)

(72) Inventors: Michael D. Pluth, Eugene, OR (US); Yu Zhao, Eugene, OR (US)

(73) Assignee: University of Oregon, Eugene, OR (US)

( * ) Notice: Subject to any disclaimer, the term of this patent is extended or adjusted under 35 U.S.C. 154(b) by 0 days.

(21) Appl. No.: 16/262,226

(22) Filed: Jan. 30, 2019

Related U.S. Application Data

(60) Provisional application No. 62/624,614, filed on Jan. 31, 2018.

(51) Int. Cl.
*C07C 333/08* (2006.01)
*G01N 33/84* (2006.01)
*C12Q 1/527* (2006.01)

(52) U.S. Cl.
CPC ............ *C07C 333/08* (2013.01); *C12Q 1/527* (2013.01); *G01N 33/84* (2013.01); *G01N 2333/988* (2013.01)

(58) Field of Classification Search
CPC ....... C07C 333/08; G01N 33/84; C12Q 1/527
See application file for complete search history.

(56) References Cited

U.S. PATENT DOCUMENTS

| | | | | |
|---|---|---|---|---|
| 7,700,560 | B2 * | 4/2010 | Creighton | C07K 5/0215 514/19.4 |
| 8,524,772 | B2 * | 9/2013 | Arad | A61K 45/06 514/547 |
| 9,630,918 | B2 * | 4/2017 | Nguyen | C07C 329/06 |
| 2002/0143202 | A1 | 10/2002 | Zhuang et al. | |
| 2007/0202198 | A1 | 8/2007 | Purcell | |
| 2007/0287672 | A1 * | 12/2007 | Creighton | A61K 31/10 424/70.11 |
| 2008/0004245 | A1 | 1/2008 | Wallace et al. | |
| 2009/0184005 | A1 | 7/2009 | Zhang et al. | |
| 2010/0099683 | A1 | 4/2010 | Tomkinson et al. | |

FOREIGN PATENT DOCUMENTS

| | | | |
|---|---|---|---|
| JP | 2737717 B2 | | 4/1998 |
| JP | 2011007937 | * | 1/2011 |
| WO | WO 2006/111791 | | 10/2006 |
| WO | WO 2012/075242 | | 6/2012 |
| WO | WO 2012/154126 | | 11/2012 |
| WO | WO 2013/045951 | | 4/2013 |
| WO | WO 2014/124205 | | 8/2014 |

OTHER PUBLICATIONS

Nazarov, CA 42:63490, abstract only of Izvestiya Akademii Nauk SSSR, Seriya Khimicheskaya, 1948, 118-126. (Year: 1948).*
Dzurilla, CA113:115217, abstract and Chemical Papers, vol. 44(1), 45-50, 1990. (Year: 1990).*
Hamilton, J Med Chem, vol. 42, 1823-1827, 1999. (Year: 1999).*
Kavarana, J Med Chem, vol. 42, 221-228, 1999. (Year: 1999).*
Rashed, Rapid Comm in Mass Spect, vol. 3(10), 360-363, 1989. (Year: 1989).*
Alajarin et al., "Benzylic Newman-Kwart rearrangement of *O*-azidobenzyl thiocarbamates triggered by phosphines: pseudopericyclic [1,3] shifts via uncoupled concerted mechanisms," *Tetrahedron*, 65(12): 2579-2590, Jan. 20, 2009.
Alajarin et al., "Intramolecular addition of benzylic radicals onto ketenimines. Synthesis of 2-alkylindoles," *Organic and Biomolecular Chemistry*, 1(23): 4282-4292, Oct. 23, 2003.
Bailey et al., "Chemiluminescent Detection of Enzymatically Produced Hydrogen Sulfide: Substrate Hydrogen Bonding Influences Selectivity for $H_2S$ over Biological Thiols," *J. Am. Chem. Soc.*, 135(44): 16697-16704, Oct. 4, 2013.
Benavides et al., "Hydrogen sulfide mediates the vasoactivity of garlic," *Proceedings of the National Academy of Sciences of the United States of America*, 104(46): 17977-17982, Nov. 13, 2007.
Braverman et al., "The Rearrangement of Furfuryl Dimethylthionocarbamates," *International Journal of Sulfur Chemistry*, 8(55): 1973.
Cerda et al "Dithioesters: simple, tunable, cysteine-selective $H_2S$ donors," Chem. Sci., Nov. 30, 2018.
Cerda et al "Thionoesters: A Native Chemical Ligation-Inspired Approach to Cysteine-Triggered H2S Donors," *J. Am. Chem. Soc.*, 2018, 140, 12574-12579, Sep. 19, 2018.
Cesarini et al., "Thiocarbamates as non-nucleoside HIV-1 reverse transcriptase inhibitors. Part 2: Parallel synthesis, molecular modelling and structure-activity relationship studies on analogues of *O*-(2-phenylethyl)-N-phenylthiocarbamate," *Biorg. Med. Chem.*, vol. 16, pp. 4173-4185, Dec. 25, 2007.
Chauhan et al., "Esterase Activated Carbonyl Sulfide/Hydrogen Sulfide ($H_2S$) Donors," *Org. Lett.*, 19(1): 62-65, Dec. 20, 2016.
Chitnis et al., "Pharmacological actions of the slow release hydrogen sulfide donor GYY4137 on phenylephrine-induced tong in isolated bovine ciliary artery," *Experimental Eye Research*, vol. 116, pp. 350-354, Nov. 2013.
Devarie-Baez et al., "Light-Induced Hydrogen Sulfide Release from 'Caged' gem-Dithiols," *Organic Letters*, 15(11): 2786-2789, May 22, 2013.
Gu et al., "Development of a boron-dipyrromethene-Cu2$^+$ ensemble based colorimetric probe toward hydrogen sulfide in aqueous media," *Tetrahedron Letters*, 52: 5000-5003, Sep. 2011.
Jarosz et al., "Microplate-Based Colorimetric Detection of Free Hydrogen Sulfide," *Analytical Chemistry*, 85(7): 3638-3643, Mar. 11, 2013.
Jensen et al., "Studies of Thioacids and Their Derivatives. IX. Thiosemicarbizides," *Acta Chemica Scandinavica*, vol. 22, pp. 1-50, 1968.

(Continued)

*Primary Examiner* — D Margaret Seaman
(74) *Attorney, Agent, or Firm* — Klarquist Sparkman, LLP

(57) ABSTRACT

Disclosed herein are embodiments of a donor compound that releases COS and/or $CS_2$, which can be converted to $H_2S$. The donor compound embodiments described herein can be used to deliver $H_2S$ to a subject or a sample and further can be used to administer therapeutic agents. Methods of making and using the donor compound embodiments also are disclosed.

14 Claims, 8 Drawing Sheets

(56) References Cited

OTHER PUBLICATIONS

Jensen et al., "Studies of Thioacids and Their Derivatives. XV. (Alkoxythiocarbonyl)hydrazines and [(Alkylthio)thiocarbonyl]hydrazines," *Acta Chemica Scandinavica*, vol. 23, pp. 1916-1934, 1969.
Kashfi et al., "Biology and therapeutic potential of hydrogen sulfide and hydrogen sulfide-releasing chimeras," *Biochemical Pharmacology*, 85(5): 689-703, Mar. 1, 2013.
Kawanaka et al., "Design and Synthesis of Orally Bioavailable Inhibitors of Inducible Nitric Oxide Synthase. Part 1: Synthesis and Biological Evaluation of Dihydropyridin-2-imines," *Bioorganic & Medicinal Chemistry Letters*, vol. 12, pp. 2291-2294, 2002.
Kim et al., "Synthesis of Novel N-(2-Hydrophenyl)arylsulfonamides as Selective HDAC Inhibitory and Cytotoxic Agents," *Bulletin of the Korean Chemical Society*, 34(5):1487-1493, 2013.
Lee et al., "Analysis of structure-activity relationships for the 'B-region' of *N*-(4-t-butylbenzyl)-*N*'-[4-(methylsulfonylamino)benzyl]-thiourea analogues as TRPV1 antagonists," *Bioorganic and Medicinal Chemistry Letters*, 15(18): 4143-4150, Sep. 15, 2005.
Lee et al., "Detection of hydrogen peroxide with chemiluminescent micelles," *International Journal of Nanomedicine*, 3(4):471-476, Dec. 2008.
Li et al., "Characterization of a novel, water-soluble hydrogen sulfide-releasing molecule (GYY4137): New insights into the biology of hydrogen sulfide," *Circulation*, 117(18): 2351-2360, May 6, 2008.
Lippert et al., "Reaction-Based Fluorescent Probes for Selective Imaging of Hydrogen Sulfide in Living Cells," *Journal of the American Chemical Society*, 133(26): 10078-10080, Jun. 15, 2011.
Liu et al., "A visible light excitable colorimetric and fluorescent ESIPT probe for rapid and selective detection of hydrogen sulfide," *Organic & Biomolecular Chemistry*, 12:438-445, Nov. 6, 2013.
Liu et al., "Capture and Visualization of Hydrogen Sulfide by a Fluorescent Probe," *Angew. Chem. Int. Ed.*, 123(44):10327-10329, Sep. 6, 2011.
Maity et al., "A probe for ratiometric near-infrared fluorescence and colorimetric hydrogen sulfide detection and imaging in living cells," *RSC Advances* vol. 4, pp. 11147-11151, Feb. 10, 2014.
Martelli et al., "Arylthioamides as H2S Donors: L-Cysteine-Activated Releasing Properties and Vascular Effects in Vitro and in Vivo," *ACS Medicinal Chemistry Letters*, 4(10): 904-908, Aug. 8, 2013.
Montoya et al., "Selective turn-on fluorescent probes for imaging hydrogen sulfide in living cells," *Chemical Communications*, vol. 48, pp. 4767-4769, Mar. 16, 2012.
Montoya et al., "Development of Selective Colorimetric Probes for Hydrogen Sulfide Based on Nucleophilic Aromatic Substitution," *J Org. Chem.*, 78(13): 6550-6557, Jun. 4, 2013.
Nishiyama et al., "Addition Reaction of Deoxygenation of Alcohols Using Isothiocyanates and Triethylsilane-DTBP," *Tetrahedron Letters*, 34(23): 3745-374, Feb. 22, 1993.
Olson et al., "A Practical Look at the Chemistry and Biology of Hydrogen Sulfide," *Antioxidants& Redox Signaling*, 17(1): 32-44, Jan. 16, 2012.
Peng et al., "A Fluorescent Probe for Fast and Quantitative Detection of Hydrogen Sulfide in Blood," *Angew. Chem. Int. Ed.*, 50(41): 9672-9675, Oct. 4, 2011.
Qian et al., "Selective fluorescent probes for live-cell monitoring of sulphide," *Nature Communications*, 2(495): 1-7, Oct. 11, 2011.
Roda et al., "Analytical chemiluminescence and bioluminescence: latest achievements and new horizons," *Analytical and Bioanalytical Chemistry*, 402(1) :69-76, Oct. 16, 2011.
Saha et al., "A colorimetric and fluorometric BODIPY probe for rapid, selective selection of $H_2S$ and its application in live cell imaging," *Organic & Biomolecular Chemistry*, vol. 11, pp. 8166-8170, Oct. 22, 2013.
Sasakura et al., "Development of a Highly Selective Fluorescence Probe for Hydrogen Sulfide," *Journal of the American Chemical Society*, 133(45): 18003-18005, Oct. 14, 2011.
Seletsky et al., "Structurally simplified macrolactone analogues of halichondrin B," *Bioorganic and Medicinal Chemistry Letters*, 14(22): 5547-5550, Sep. 21, 2004.
Shen et al., "Measurement of plasma hydrogen sulfide in vivo and in vitro," *Free Radical Biology & Medicine*, 50(9): 1021-1031, Jan. 27, 2011.
Tomasova et al., "Effects of AP39, a novel triphenylphosphonium derivatised anethole dithioethione hydrogen sulfide donor, on rat haemodynamic parameters and chloride and calcium Ca(v)3 and RyR2 channels," *Nitric Oxide-Biology and Chemistry*, vol. 46, pp. 131-144, Dec. 30, 2014.
Van De Bittner et al., "In vivo imaging of hydrogen peroxide production in a murine tumor model with a chemoselective bioluminescent reporter," *PNAS*, 107(50):21316-21321, Dec. 14, 2010.
Wei et al., "NBD-based colorimetric and fluorescent turn-on probes for hydrogen sulfide," *Organic & Biomolecular Chemistry*, vol. 12, pp. 479-485, Oct. 29, 2013.
Whiteman et al., "Emerging role of hydrogen sulfide in health and disease: critical appraisal of biomarkers and pharmacological tools," *Clinical Science*, 121(11): 459-488, Aug. 9, 2011.
Wu et al., "A selective colorimetric and ratiometric fluorescent probe for hydrogen sulfide," *Organic & Biomolecular Chemistry*, vol. 10, pp. 8342-8347, Aug. 8, 2012.
Yamaguchi et al., "Evaluation of chemiluminescence reagents for selective detection of reactive oxygen species," *Analytica Chimica Acta*, 665(1): 74-78, Mar. 19, 2010.
Yu et al., "Study on Cyclometalated Palladium-azo Complexes as Colorimetric Probes for Hazardous Gas in Water," *Chinese J. Chem.*, 25(6): 797-801, Jun. 14, 2007.
Zhang et al., "A dicopper complex chemiluminescence probe for the determination of thiols in the extracts of murine P388 lymphocytic leukemia cell," *Chem. Comm.*, No. 37, pp. 5624-5626, Aug. 18, 2009.
Zhang et al., "Highly selective and sensitive colorimetric probe for hydrogen sulfide by a copper (II) complex of azo-dye based on chemosensing ensemble approach," *Spectrochimica Acta Part A: Molecular and Biomolecular Spectroscopy*, vol. 90, pp. 35-39, Jan. 16, 2012.
Zhang et al., "On-Site Visual Detection of Hydrogen Sulfide in Air Based on Enhancing the Stability of Gold Nanoparticles," *ACS Applied Materials & Interfaces*, 6(9):6300-6307, Apr. 22, 2014.
Zhao et al. "Colorimetric Carbonyl Sulfide (COS)/Hydrogen Sulfide ($H_2S$) Donation from g-Ketothiocarbamate Donor Motifs," Angew. Chem. Int. Ed. Oct. 1, 2018.
Zhao et al., "A highly selective colorimetric chemodosimeter for fast and quantitative detection of hydrogen sulfide," *Analyst*, 137(23):5576-5580, Sep. 25, 2012.
Zhao et al., "Cysteine-Activated Hydrogen Sulfide (H2S) Donors," *Journal of the American Chemical Society*, 133(1): 15-17, Jan. 12, 2011.
Zhou et al., "Thioglycine and L-thiovaline: Biologically active H2S-donors," *Bioorganic & Medicinal Chemistry*, 20(8): 2675-2678, Feb. 27, 2012.

* cited by examiner

COMPOUND EMBODIMENTS FOR HYDROGEN SULFIDE PRODUCTION AND METHODS OF MAKING AND USING THE SAME

CROSS REFERENCE TO RELATED APPLICATION

This application claims the benefit of the earlier filing date of U.S. Provisional Patent Application No. 62/624,614, filed on Jan. 31, 2018; this prior application is incorporated herein by reference in its entirety.

ACKNOWLEDGMENT OF GOVERNMENT SUPPORT

This invention was made with government support under Contract No. R01GM113030 awarded by the National Institutes of Health. The government has certain rights in the invention.

FIELD

Disclosed herein are embodiments of a donor compound that can be triggered to release carbonyl sulfide ("COS") or carbon disulfide ("$CS_2$")—both of which can be converted to hydrogen sulfide ("$H_2S$")—as well as embodiments of methods for making and using the donor compound embodiments.

BACKGROUND

Hydrogen sulfide has been recognized as an important biological molecule and plays important biological and pharmacological roles in different conditions associated with human health. For example, $H_2S$ has been implicated in hypertension, diabetes, diseases of mental deficiency, asthma, stroke, and other conditions. For example, administration of $H_2S$ results in reduction in blood pressure in hypertensive mice.

Although convenient, direct administration of $H_2S$ or sulfide-containing salts leads to a large burst of released $H_2S$, which is quickly metabolized/oxidized by cellular components as part of a toxicological response, and merely results in a disruption of redox homeostasis rather than elevated $H_2S$ levels. There exists a need in the art for an $H_2S$ delivery platform that provides the ability to control the amount and speed of $H_2S$ delivery.

SUMMARY

Disclosed herein are embodiments of a donor compound. The donor compound embodiments are capable of releasing COS and/or $CS_2$ and thus can act as $H_2S$ donors. The structure of these donor compound embodiments are described herein. Also disclosed herein are embodiments of a pharmaceutical composition comprising donor compound embodiments described herein, as well as a composition comprising products obtained from deprotonation of the donor compound embodiments. Further disclosed are embodiments of a method for using the donor compounds, such as method embodiments for treating a subject that has or is at risk of developing a disease associated with $H_2S$ deficiency or $H_2S$ misregulation and/or a disease associated with carbonic anhydrase overexpression.

The foregoing and other objects, features, and advantages of the present disclosure will become more apparent from the following detailed description, which proceeds with reference to the accompanying figures.

BRIEF DESCRIPTION OF THE DRAWINGS

FIG. 10 is a bar graph showing results from assessing the cytotoxicity of γ-KetoTCM-1 (bars labeled with "a"), γ-KetoCM-1 (bars labeled with "b"), and γ-KetoTCM-3 (bars labeled with "c") in RAW 264.7 cells, wherein =P<0.01 vs VEH group and *=P<0.001 vs VEH group.

DETAILED DESCRIPTION

I. Overview of Terms

Figure 1A:
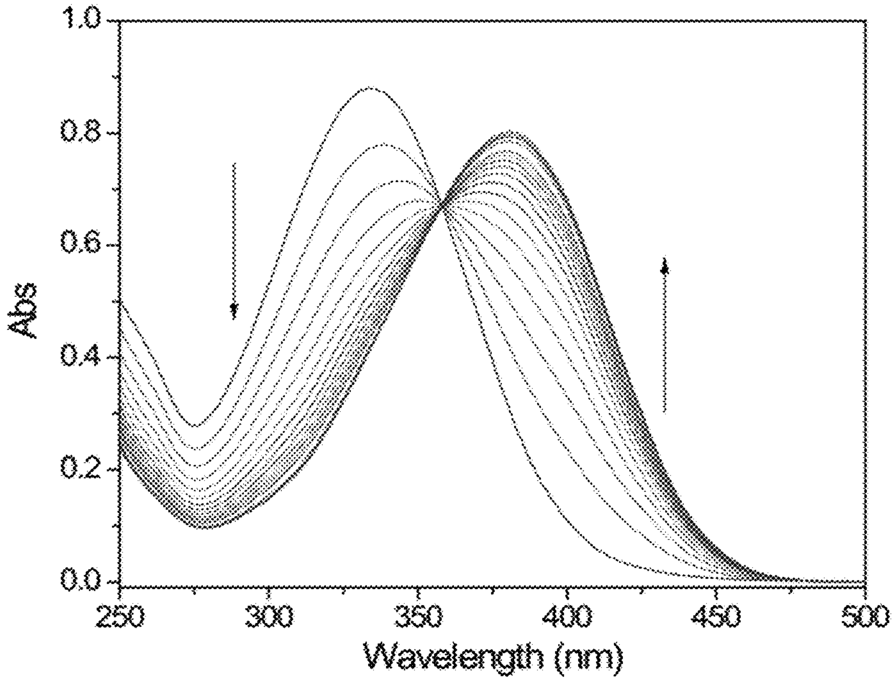
FIG. 1A is a graph of absorbance as a function of wavelength (nm) providing UV-Vis spectra of p-nitroaniline formation from a donor compound embodiment, γ-KetoTCM-1.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a symbol "-" which is used to show how the defined functional group attaches to, or within, the donor compound to which it is bound. Also, a dashed bond (i.e., "- - - ") as used in certain formulas described herein indicates an optional bond (that is, a bond that may or may not be present). A person of ordinary skill in the art would recognize that the definitions provided below and the donor compounds and formulas included herein are not intended to include impermissible substitution patterns (e.g., methyl substituted with 5 different groups, and the like). Such impermissible substitution patterns are easily recognized by a person of ordinary skill in the art. In formulas and donor compounds disclosed herein, a hydrogen atom is present and completes any formal valency requirements (but may not necessarily be illustrated) wherever a functional group or other atom is not illustrated. For example, a phenyl ring that is drawn as

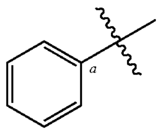 [SMILES: *c1ccccc1]

comprises a hydrogen atom attached to each carbon atom of the phenyl ring other than the "a" carbon, even though such hydrogen atoms are not illustrated. Any functional group disclosed herein and/or defined above can be substituted or unsubstituted, unless otherwise indicated herein.

Acyl Halide: —C(O)X, wherein X is a halogen, such as Br, F, I, or Cl.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Aliphatic-aryl: An aryl group that is or can be coupled to a compound disclosed herein, wherein the aryl group is or becomes coupled through an aliphatic group.

Aliphatic-heteroaryl: A heteroaryl group that is or can be coupled to a compound disclosed herein, wherein the heteroaryl group is or becomes coupled through an aliphatic group.

Alkenyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or 4.

Alkoxy: —O-aliphatic, with exemplary embodiments including, but not limited to, methoxy, ethoxy, n-propoxy, isopropoxy, n-butoxy, t-butoxy, sec-butoxy, n-pentoxy.

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkyl-aryl/Alkenyl-aryl/Alkynyl-aryl: An aryl group that is or can be coupled to a compound disclosed herein, wherein the aryl group is or becomes coupled through an alkyl, alkenyl, or alkynyl group, respectively.

Alkyl-heteroaryl/Alkenyl-heteroaryl/Alkynyl-heteroaryl: A heteroaryl group that is or can be coupled to a compound disclosed herein, wherein the heteroaryl group is or becomes coupled through an alkyl, alkenyl, or alkynyl group, respectively.

Alkynyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —C(O)NR$^a$R$^b$ or NHCOR$^a$ wherein each of R$^a$ and R$^b$ independently is selected from hydrogen, aliphatic, heteroaliphatic, haloaliphatic, haloheteroaliphatic, aromatic, or any combination thereof.

Amine: —NR$^a$R$^b$, wherein each of R$^a$ and R$^b$ independently is selected from hydrogen, aliphatic, heteroaliphatic, haloaliphatic, haloheteroaliphatic, aromatic, or any combination thereof.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system.

Typically, the number of out of plane n-electrons corresponds to the Hückel rule (4n+2). The point of attachment to the parent structure is through an aromatic portion of the condensed ring system. For example,

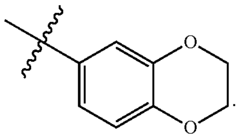 [SMILES: *c1ccc2c(c1)OCCO2]

However, in certain examples, context or express disclosure may indicate that the point of attachment is through a non-aromatic portion of the condensed ring system. For example,

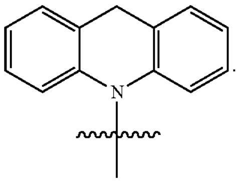 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, aromatic, other functional groups, or any combination thereof.

Carboxyl: —C(O)OH or an anion thereof.

Detectable signal: A signal (e.g., a color change, an increase or decrease in fluorescence, an increase or decrease in phosphorescence or other type of luminescence, and the like) that occurs when a donor compound disclosed herein comprising a detectable moiety (e.g., a fluorophore or a dye) is exposed to conditions effective to promote a deprotonation and elimination sequence of the donor compound.

Disulfide: —SSR$^a$, wherein R$^a$ is selected from hydrogen, aliphatic, heteroaliphatic, haloaliphatic, haloheteroaliphatic, aromatic, or any combination thereof.

Electron-Donating Group: A functional group capable of donating at least a portion of its electron density into the ring to which it is directly attached, such as by resonance. Representative and non-limiting examples of electron-donating groups can include alkoxy, thioether, amine (e.g., primary, secondary, or tertiary amine), hydroxyl, thiol, ether, acyloxy, aliphatic (e.g., alkyl, alkenyl, or alkynyl), aryl, aliphatic-aryl, heteroaliphatic-aryl.

Electron-Withdrawing Group: A functional group capable of accepting electron density from the ring to which it is directly attached, such as by inductive electron withdrawal. Representative and non-limiting examples of electron-withdrawing groups can include aldehyde, ketone, ester, carboxylic acid, acyl, a quaternary amine, acyl halide, cyano, sulfonate, nitro, nitroso, pyridinyl, alkyl halide, halogen (e.g., chloro, bromo, fluoro, or iodo), haloaliphatic, ammonium, or amide.

Ester: —C(O)OR$^a$ wherein R$^a$ is aliphatic, heteroaliphatic, haloaliphatic, haloheteroaliphatic, aromatic, or any combination thereof; or —OC(O)R$^a$, wherein R$^a$ is selected from hydrogen, aliphatic, heteroaliphatic, haloaliphatic, haloheteroaliphatic, aromatic, or any combination thereof.

Fluorophore: A functional group or portion of a donor compound disclosed herein that causes the donor compound or a heteroatom-terminated group to fluoresce when exposed to an excitation source. Exemplary fluorophores are described herein.

Haloaliphatic: An aliphatic group wherein one or more hydrogen atoms, such as one to 10 hydrogen atoms, independently is replaced with a halogen atom, such as fluoro, bromo, chloro, or iodo.

Haloaliphatic-aryl: An aryl group that is or can be coupled to a compound disclosed herein, wherein the aryl group is or becomes coupled through a haloaliphatic group.

Haloaliphatic-heteroaryl: A heteroaryl group that is or can be coupled to a compound disclosed herein, wherein the heteroaryl group is or becomes coupled through a haloaliphatic group.

Haloakyl: An alkyl group wherein one or more hydrogen atoms, such as one to 10 hydrogen atoms, independently is replaced with a halogen atom, such as fluoro, bromo, choro, or iodo. In an independent embodiment, haloalkyl can be a $CX_3$ group, wherein each X independently can be selected from fluoro, bromo, choro, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group.

Heteroaliphatic-aryl: An aryl group that is or can be coupled to a compound disclosed herein, wherein the aryl group is or becomes coupled through a heteroaliphatic group.

Heteroalky/Heteroakenyl/Heteroakynyl: An alkyl, alkenyl, or alkyny group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group.

Heteroalkyl-aryl/Heteroalkenyl-aryl/Heteroakynyl-aryl: An aryl group that is or can be coupled to a compound disclosed herein, wherein the aryl group is or becomes coupled through a heteroalkyl, heteroalkenyl, or heteroalkyny group, respectively.

Heteroalkyl-heteroaryl/Heteroalkenyl-heteroaryl/eteroalkynyl-heteroary: A heteroaryl group that is or can be coupled to a compound disclosed herein, wherein the heteroaryl group is or becomes coupled through a heteroalkyl, heteroalkenyl, or heteroalkynyl group, respectively.

Heteroaryl: An aryl group comprising at least one heteroatom to six heteroatoms, such as one to four heteroatoms, which can be selected from, but not limited to oxygen, nitrogen, sulfur, silicon, boron, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. Heteroaryl groups may be substituted with one or more groups other than hydrogen, such as aliphatic, heteroaliphatic, aromatic, other functional groups, or any combination thereof.

Heteroatom: An atom other than carbon, such as oxygen, nitrogen, sulfur, silicon, boron, selenium, or phosphorous. In particular disclosed embodiments, such as when valency constraints do not permit, a heteroatom does not include a halogen atom.

Heteroatom-Terminated Compound: A compound produced from a donor compound by an elimination reaction (or elimination step) caused by exposing donor compound embodiments to conditions effective to deprotonate a hydrogen atom of the donor compound and facilitate elimination or release of the heteroatom-terminated compound. In some embodiments, the heteroatom-terminated compound can comprise the V or V—$R^1$ group of the formulas described herein after breaking the bond between the V or V—$R^1$ group and the carbon atom to which it is bound, wherein V is an oxygen atom, a nitrogen atom, a sulfur atom, or other heteroatom, the heteroatom-terminated compound further comprising the $R^2$ group bound to V in the formulas described herein.

Ketone: —C(O)$R^a$, wherein $R^a$ is selected from aliphatic, heteroaliphatic, aromatic, any combination thereof.

Pharmaceutically Acceptable Excipient: A substance, other than a donor compound that is included in a formulation of the donor compound. As used herein, an excipient may be incorporated within particles of a pharmaceutical composition, or it may be physically mixed with particles of a pharmaceutical composition. An excipient also can be in the form of a solution, suspension, emulsion, or the like. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropy cellulose, hydroxypropy methylcellulose, xylitol, sorbitol, maltitol, gelatin, polyvinylpyrrolidone (PVP), polyethylene glycol (PEG), tocopheryl polyethyene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methy paraben, propyl paraben, sugar, silica, talc, magnesium carbonate, sodium starch glycolate, tartrazine, aspartame, benzalkonium chloride, sesame oil, propyl gallate, sodium metabisulphite or lanolin. In independent embodiments, water is not intended as a pharmaceutically acceptable excipient.

Silyl Ether: A functional group comprising a silicon atom covalently bound to an alkoxy group.

Solubilizing Agent: An agent that increases the solubility of a donor compound disclosed herein in aqueous media. Solubilizing agents can be selected from, but are not limited to, sodium bicarbonate, glucose, polyalkylene ethers or glycols (e.g., polyethylene glycol, polypropylene glycol, and the like), surfactants (e.g., sorbitan esters), and other solubilizing agents known in the art.

Subject: Mammals and other animals, such as humans, companion animals (e.g., dogs, cats, rabbits, etc), utility animals, and feed animals; thus, disclosed methods are applicable to both human therapy and veterinary applications.

Sulfonyl/Sulfonate: —$SO_2R^a$, wherein $R^a$ is selected from hydrogen, aliphatic, heteroaliphatic, haloaliphatic, haloheteroaliphatic, aromatic, and any combination thereof.

Targeting Group: A group that is capable of targeting a cell, an organelle, or the like and thereby directing the donor compound comprising the targeting group to the cell, organelle, or the like. In some embodiments, a targeting group can be morpholine or a derivative thereof, a phosphonium or phosphine group, a quaternary amine, or the like. Other targeting components can include thiol or hydroxyl functional groups, which can be used to target surfaces or monolayers.

Treating/Treatment: Treatment of a disease or condition of interest in a subject, particularly a human or canine having the disease or condition of interest, and includes by way of example, and without limitation:

(i) prophylactic administration to prevent the disease or condition from occurring in a subject, or to ameliorate symptoms associated with the condition if required in particular, when such subject is predisposed to the condition but has not yet been diagnosed as having it;

(ii) inhibiting the disease or condition, for example, arresting or slowing its development;

(iii) relieving the disease or condition, for example, causing regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

II. Introduction

Described herein are embodiments of a novel donor compound that provides triggerable carbonyl sulfide (or "COS") and/or carbon disulfide (or "$CS_2$") release. As such, the donor compound embodiments described herein are capable of releasing $H_2S$ because the released COS or $CS_2$ can readily be converted to $H_2S$. Without intending to be limited to a particular theory, it currently is believed that donor compound embodiments described herein can be deprotonated, which results in an elimination cascade whereby COS or $CS_2$ is released from the compound. The donor compound embodiments also can be functionalized with a detectable moiety capable of producing a detectable signal and/or a therapeutic agent, targeting agent, sugar, or the like. In some embodiments, the donor compound can release carbonyl sulfide (COS), which is rapidly converted to $H_2S$ by the ubiquitous enzyme carbonic anhydrase (CA), water, or a combination thereof. In yet additional embodiments, the donor compound can release carbon disulfide ($CS_2$), which can be converted to $H_2S$ using water or enzymes, such as nitrogenase, RuBisCO, CO dehydrogenase, COSase, $CS_2$ hydrolase, or any combination thereof.

The donor compound embodiments described herein are highly modular, allowing for both the triggering moieties and the rate of $H_2S$ release (by way of COS and/or $CS_2$ release) from the compound to be readily modified as well as allowing the ability to tune the functionality of the compound (such as to provide a detectable signal and/or a therapeutic agent, targeting agent, sugar, or the like). The donor compound embodiments also are stable against nucleophilic attack, such as from biological nucleophiles (e.g., cysteine, homocysteine, glutathione, and the like). As such, the donor compound embodiments are able to avoid premature and/or undesired release of COS and/or $CS_2$.

The donor compound embodiments of the present disclosure are not only useful research tools, but also have many therapeutic applications, such as providing a platform for protection in a subject with high, eminent MI markers and/or delivering therapeutic agents simultaneously with COS and/or $CS_2$ release. There are a number of diseases, such as glaucoma, that are characterized by an over-expression of CA but which can also be treated by $H_2S$ addition. Diseases that are linked to $H_2S$ deficiency and/or that can be treated with $H_2S$ are particularly attractive diseases to treat using the donor compound embodiments described herein. In some embodiments, the disease can include cardiovascular diseases (e.g., heart failure, myocardial reperfusion injury, atherosclerosis, hypertension, hypertrophy), diabetes, inflammation, neurological diseases, cancer, wound healing, erectile dysfunction, as well as other conditions and diseases. The compound embodiments disclosed herein also can be functionalized with a therapeutic agent and as such can be used as therapeutic delivery agents at the same time as serving as $H_2S$ providers.

Compound embodiments disclosed herein address a large challenge in the field of $H_2S$ research: namely that the amount of $H_2S$ released from synthetic donors known in the art can vary depending on the local environment, thus making it difficult to correlate release rates in different environments. The colorimetric readout provided by compound embodiments of the present disclosure facilitate real-time tracking of $H_2S$ release using UV-vis spectroscopy.

III. Compound Embodiments

Disclosed herein are embodiments of a donor compound that can be used to trigger $H_2S$ production. Such donor compound embodiments comprise an active hydrogen atom that can be deprotonated to facilitate an elimination cascade whereby COS or $CS_2$ is released. The released COS or $CS_2$ can both be further converted to $H_2S$ in situ or upon exposure to a suitable conversion component, which is described herein. In some embodiments, a detectable moiety and/or a component comprising a therapeutic agent, a targeting agent, sugar, or the like also can be released from the compound. In some embodiments, the donor compound can have structure satisfying Formula 1. In particular embodiments, the active hydrogen atom is located in the β position, as illustrated in Formula 1.

Formula 1

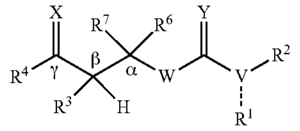

With reference to Formula 1, the following variable recitations can apply in any combination:

X can be selected from oxygen, sulfur, NR' or $N^+(R')_2$, wherein each R' independently is hydrogen, aliphatic, haloaliphatic, haloheteroaliphatic, heteroaliphatic, aromatic, or any combination thereof;

each of W and Y independently can be selected from oxygen or sulfur; V is a heteroatom and in some embodiments is oxygen, sulfur, or nitrogen (wherein the nitrogen atom is further bound to $R^1$);

$R^1$, if present (such as when V is nitrogen), can be selected from hydrogen, aliphatic, haloaliphatic, haloheteroaliphatic, heteroaliphatic, aromatic, or any combination thereof;

$R^2$ can be selected from aliphatic, aromatic, heteroaliphatic; or $R^1$ and $R^2$ when taken together with V can be a heteroaliphatic group, such as a heterocyclic group;

$R^3$ can be hydrogen, halogen, aliphatic, haloaliphatic, haloheteroaliphatic, heteroaliphatic, aromatic, or any combination thereof;

$R^4$ can be hydrogen, halogen, aliphatic, haloaliphatic, haloheteroaliphatic, heteroaliphatic, aromatic, or any combination thereof; and each of $R^6$ and $R^7$ independently can be hydrogen, aliphatic, haloaliphatic, haloheteroaliphatic, heteroaliphatic, aromatic, or any combination thereof.

In an independent embodiment, if W is oxygen, then Y is not, or is other than, oxygen.

In some embodiments, $R^2$ taken together with V (and $R^1$ when present) can be a component that produces a detectable signal upon elimination from the compound. In some embodiments, $R^2$ can be a group described above that further comprises a therapeutic agent. In particular disclosed embodiments, $R^2$ and $R^1$ together with V can be heterocyclic group, such as a 4-, 5-, 6-, or 7-membered heterocyclic group, which can (but need not) comprise one or more heteroatoms in addition to V. In particular disclosed embodiments, $R^2$ can be a quantum dot, a fluorophore selected from a xanthene derivative (e.g., fluorescein, rhodamine, eosin, Texas red, Oregon green, or the like), cyanine or a cyanine derivative (e.g., indocarbocyanine, oxacarbocyanine, thiacarbocyanine, merocyanine, Cy3, or Cy5), a naphthalene derivative (e.g., dansyl, prodan, and the like), coumarin and derivatives thereof (e.g., hydroxycoumarin, aminocoumarin, methoxycoumarin, and the like), oxadiazole derivatives (e.g., pyridyoxazole, nitrobenzoxadiazole, benzoxadiazole, and the like), anthracene derivatives, pyrene derivatives (e.g., cascade blue), oxazine derivatives (e.g., Nile red, Nile blue, cresyl violet, and the like), acridine derivatives (e.g., auramine, crystal violet, malachite green, and the like), fluorone dyes (e.g., rhodamine, rhodol, methylrhodol), isoquinoline dyes (e.g., 2-(2-methoxyethyl)-1H-benzo[de]isoquinoline-1,3(2H)-dione), a naphthalimide compound (e.g., naphthalimide or 4-(2-methoxyethoxy)-N-butyl-1,8-naphthalimide), a chromenone dye (e.g., 4-methy-2H-chromen-2-one), and tetrapyrrole derivatives (e.g., porphin, phthalocyanine, and the like), or a precursor thereof. In particular disclosed embodiments $R^2$ can be methylrhodol, 2-(2-methoxyethyl)-1H-benzo[de]isoquinoline-1,3(2H)-dione, 4-methyl-2H-chromen-2-one, coumarin, naphthalimide, fluorescein, rhodamine, rhodol, Cy3, or Cy5, wherein V (or V—$R^1$) can be attached at any suitable position to such fluorophores as long as the presence of V (or V—$R^1$) or the position to which V (or V—$R^1$) is bound does not deleteriously effect the detectable signals produced by such compounds.

In particular disclosed embodiments, the following substituent recitations can apply to Formula I in any combination:

X is oxygen, sulfur, or NR' or N+$(R')_2$, wherein each R' independently is hydrogen, alkyl, alkenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alky-aryl/alkenyl-aryl/alkynyl-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkynyl-heteroaryl or any combination thereof;

W is oxygen when Y is sulfur, or W is sulfur when Y is oxygen, or W is sulfur when Y is sulfur;

Y is oxygen when W is sulfur, or Y is sulfur when W is oxygen, or Y is sulfur when W is sulfur;

V is oxygen, sulfur, or nitrogen (wherein if V is nitrogen, then the dashed bond of Formula 1 represents a bond between $R^1$ and the nitrogen atom; or if V is oxygen or sulfur, then the dashed bond and $R^1$ are not present);

$R^1$, if present (such as when V is nitrogen) is hydrogen, alkyl, alkenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-aryl/alkenyl-aryl/alkyny-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkyny-heteroaryl, or any combination thereof;

$R^2$ is aliphatic; heteroaliphatic; aliphatic-aromatic; heteroaliphatic-aromatic; aromatic; -aromatic-$(R^5)_m$, wherein m can be an integer ranging from 0 to an integer value equal to the number of positions on the aromatic group that can be substituted and in some embodiments is an integer ranging from 0-5 (e.g., 0, 1, 2, 3, 4, or 5); and each $R^5$ independently is an electron-donating group, an electron-withdrawing group, or a therapeutic agent, such as an anti-inflammation drug (e.g., naproxen or other NSAID) or other small molecule therapeutics; or any combination thereof;

$R^3$ is hydrogen, Cl, F, Br, I, alkyl, alkenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alky-aryl/alkenyl-aryl/alkyny-aryl, alky-heteroaryl/alkenyl-heteroaryl/alkynyl-heteroaryl, heteroalkyl-aryl/heteroalkenyl-aryl/heteroalkyny-aryl, heteroalkyl-heteroaryl/heteroalkenyl-heteroaryl/heteroalkyny-heteroaryl, or any combination thereof;

$R^4$ is hydrogen, Cl, F, Br, I, alkyl, alkenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-aryl/alkenyl-aryl/alkyny-aryl, alky-heteroaryl/alkenyl-heteroaryl/alkynyl-heteroaryl, heteroalkyl-aryl/heteroalkenyl-aryl/heteroalkynyl-aryl, heteroakyl-heteroaryl/heteroalkenyl-heteroaryl/heteroalkyny-heteroaryl, or any combination thereof; and $R^6$ and $R^7$ independently are hydrogen, C, F, Br, I, alkyl, alkenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-aryl/alkenyl-aryl/alkyny-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkyny-heteroaryl, or any combination thereof.

In yet some additional embodiments, the following substituent recitations can apply to Formula I in any combination:

X is oxygen or sulfur;

W is oxygen when Y is sulfur, or W is sulfur when Y is oxygen, or W is sulfur when Y is sulfur Y is oxygen when W is sulfur, or Y is sulfur when W is oxygen, or Y is sulfur when W is sulfur;

V is oxygen, sulfur, or nitrogen (wherein if V is nitrogen, then the dashed bond of Formula 1 represents a bond between $R^1$ and the nitrogen atom; or if V is oxygen or sulfur, then the dashed bond and $R^1$ are not present);

$R^1$, if present (such as when V is nitrogen) is hydrogen or lower alkyl;

$R^2$ is aryl; heteroaryl; aliphatic-aryl; aliphatic-heteroaryl; heteroaliphatic-aryl; heteroaliphatic-heteroaryl; or aliphatic-aryl-$(R^5)_m$, aliphatic-heteroaryl-$(R^5)_m$, heteroaliphatic-aryl-$(R^5)_m$, heteroaliphatic-heteroaryl-$(R^5)_m$, aryl-$(R^5)_m$ or heteroaryl-$(R^5)_m$ wherein m can be an integer selected from 0-5 and each $R^5$ independently is aldehyde, ketone, ester (—$COOR^a$ or —$OCOR^a$), carboxylic acid, acyl, acyl halide, cyano, sulfonate, nitro, nitroso, pyridinyl, alky halide, halogen (e.g., chloro, bromo, fluoro, or iodo), haloaliphatic, ammonium, amide (—$CONH_2$ or —$NHCOR^a$), alkoxy, thioether, amine (e.g., primary, secondary, tertiary, or quaternary amine), hydroxyl, thiol, ether, acyloxy, aliphatic (e.g., alkyl, alkenyl, alkyny), aryl, aliphatic-aryl, heteroaliphatic-aryl, an NSAID or other therapeutic agent, or any combinations thereof; and in some embodiments when the heteroaryl group or the aryl group is a 6-membered ring, $R^5$ can be in the ortho, meta, or para position relative to the bond between the $R^2$ group and the remainder of Formula 1;

$R^3$ is hydrogen or lower alky (e.g., $C_{1-10}$);

$R^4$ is hydrogen, lower alkyl (e.g., $C_{1-10}$), an ester (—$OCOR^a$), or thioester (—$SCOR^a$); and $R^6$ and $R^7$ independently are hydrogen or lower alkyl(e.g., $C_{1-10}$).

In some embodiments, the donor compound can have a structure satisfying any one of Formulas 2A-2I below. With reference to these formulas, each of $R^1$, $R^2$, $R^3$, $R^4$, $R^6$, and $R^7$ can be as recited above for Formula 1.

Formula 2A

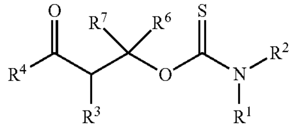

Formula 2B

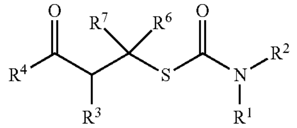

-continued

Formula 2C

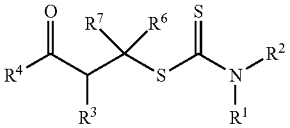

Formula 2D

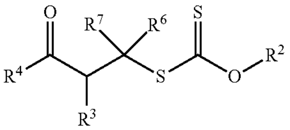

Formula 2E

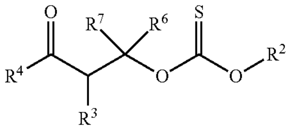

Formula 2F

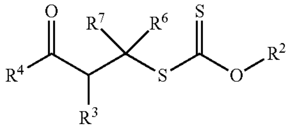

Formula 2G

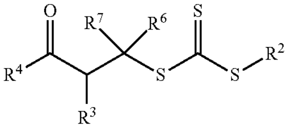

Formula 2H

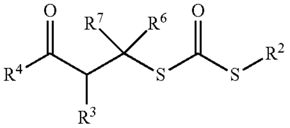

Formula 2I

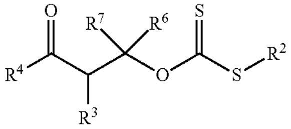

In yet some additional embodiments, the donor compound can have a structure satisfying any one of Formulas 3A-3I, illustrated below. With reference to these formulas, each of $R^1$, $R^2$, $R^3$, $R^4$, $R^5$, $R^6$, $R^7$, and m can be as recited above for Formula 1; ring A can be an aromatic group, an aliphatic-aromatic group, or a heteroaliphatic-aromatic group.

Formula 3A

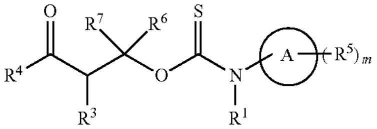

Formula 3B

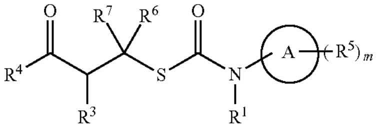

-continued

Formula 3C

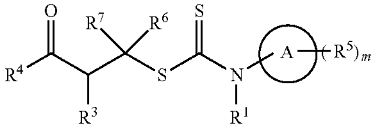

Formula 3D

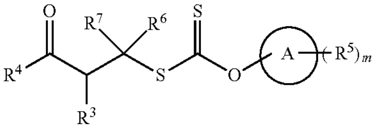

Formula 3E

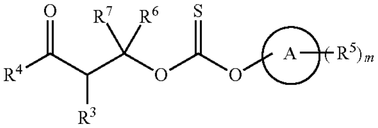

Formula 3F

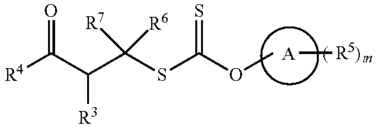

Formula 3G

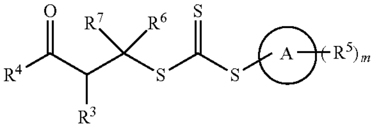

Formula 3H

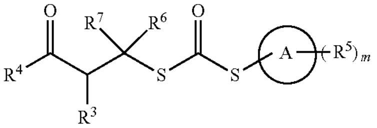

Formula 3I

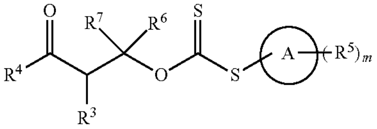

Representative donor compound embodiments are illustrated below:

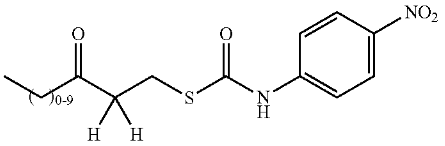

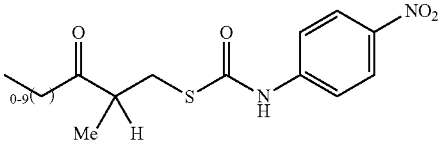

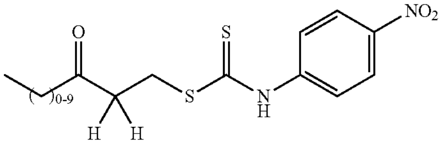

-continued
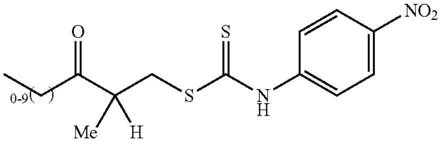
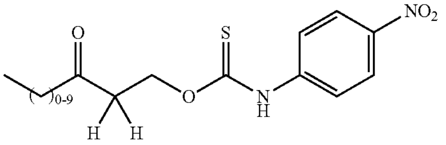
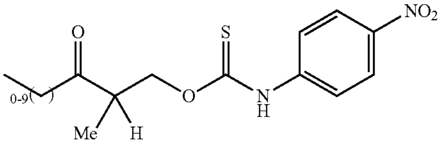
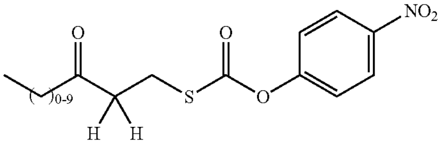
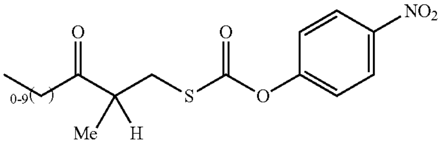
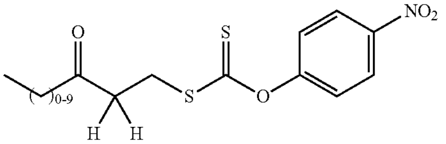
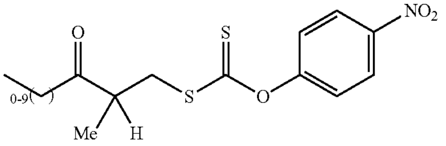
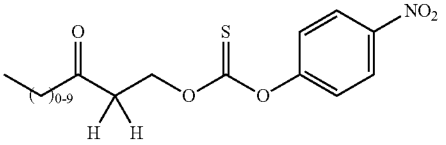
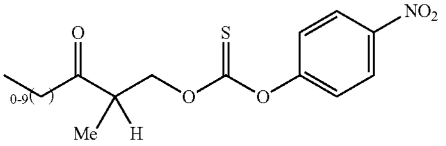
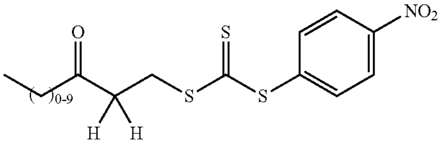
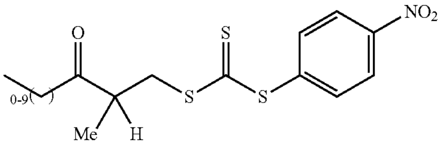
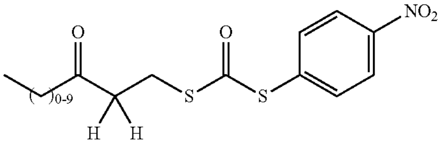
-continued
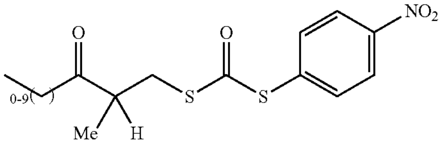
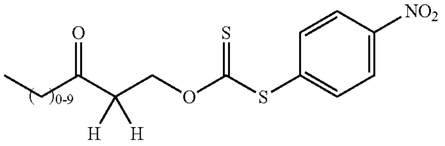
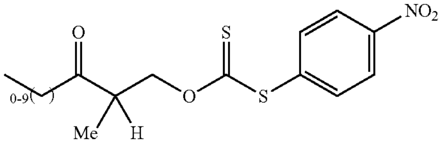
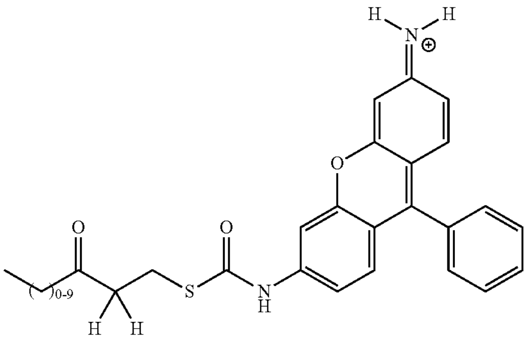
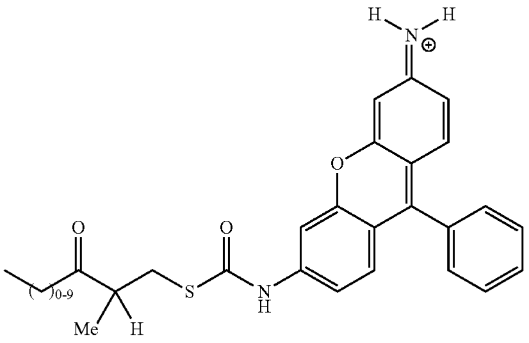
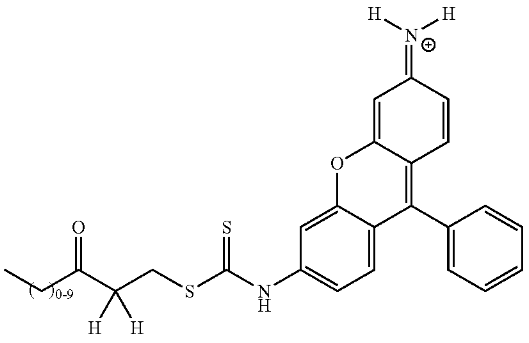

-continued
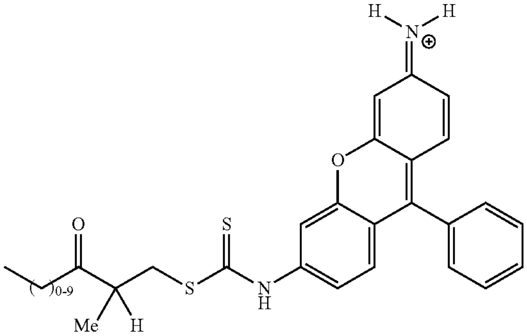
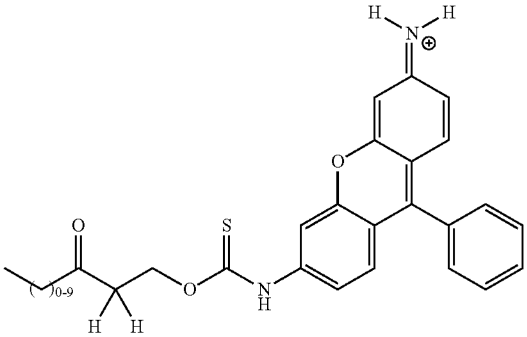
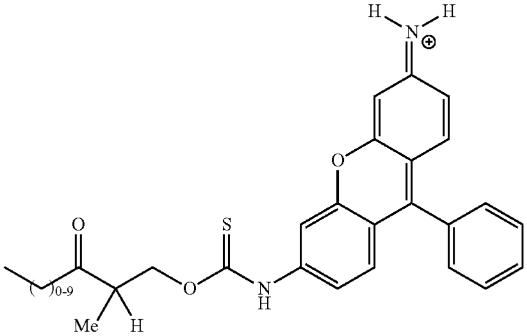
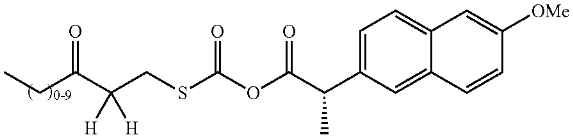
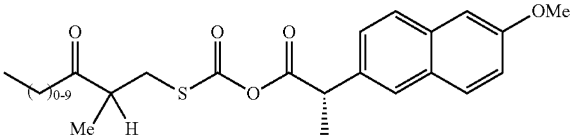
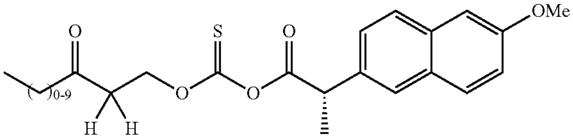
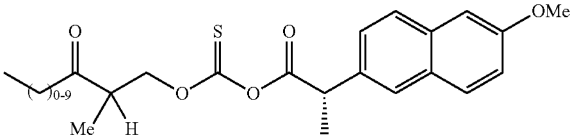
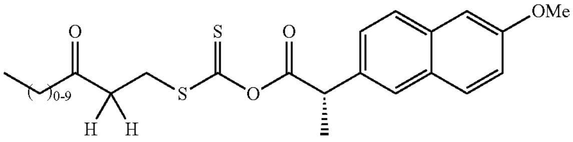
-continued
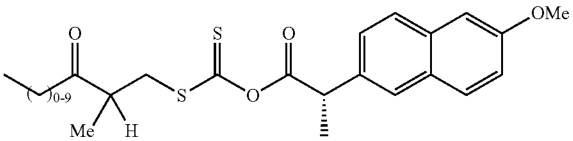
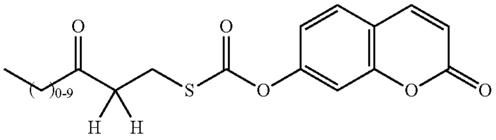
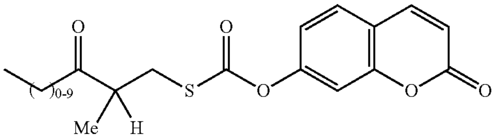
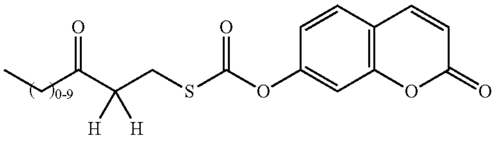
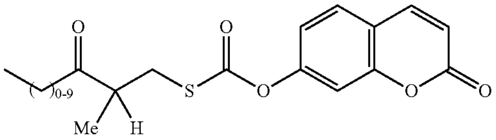
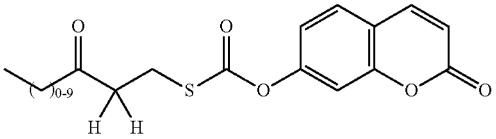
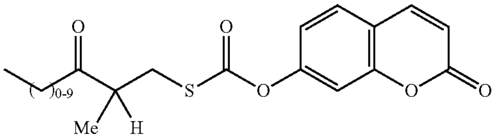
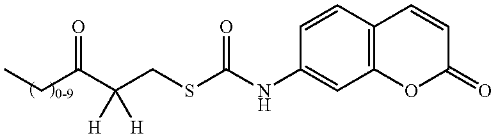
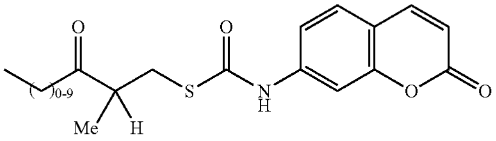
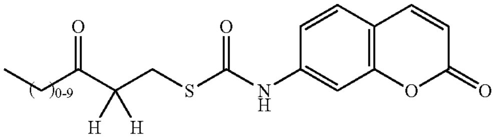
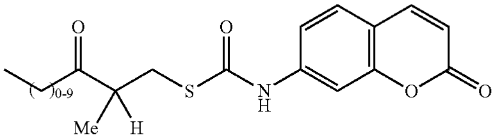
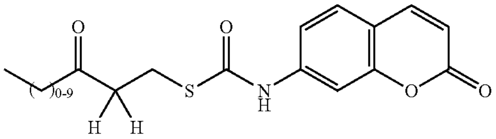

-continued

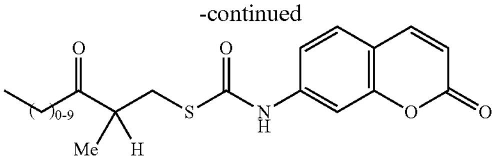

Composition embodiments comprising a donor compound also are disclosed herein. In some embodiments, the composition comprises a donor compound embodiment, or a plurality thereof. In some embodiments, the composition can further comprise water, a buffer, or any combination thereof. In some embodiments, the composition can be a pharmaceutical composition that comprises a donor compound and one or more pharmaceutically acceptable excipients, water, a pharmaceutically acceptable buffer, a separate therapeutic agent, or any combinations thereof. In some embodiments, the pharmaceutical composition comprises a donor compound comprising a therapeutic agent, such as certain donor compound embodiments described above.

Also disclosed herein are embodiments of a composition comprising one or more products formed from a donor compound after deprotonation. Such composition embodiments also can comprise an amount of the donor compound, such as amounts of any unreacted donor compound embodiment. In particular disclosed embodiments, the composition can comprise a heteroatom-terminated compound, COS, $CS_2$, $H_2S$, an olefin-containing compound, a conversion component (such as a component that promotes or facilitates conversion of COS and/or $CS_2$ to $H_2S$), or any combination thereof. In some embodiments, the composition comprises a heteroatom-terminated compound. In additional embodiments, the composition comprises COS, $CS_2$, $H_2S$ or any combination thereof. In yet additional embodiments, the composition comprises an olefin-containing compound having a structure satisfying Formula 4. With reference to Formula 4, each of X, $R^3$, $R^4$, $R^5$, and $R^7$ can be as recited above for Formula 1. In particular disclosed embodiments, X is oxygen or sulfur, $R^3$ is aliphatic, $R^4$ is aliphatic, and $R^6$ and $R^7$ are hydrogen.

Formula 4

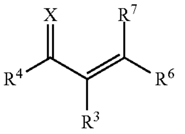

In some embodiments, the composition comprises a heteroatom-terminated compound, COS, and an olefin-containing compound. In some embodiments, the composition comprises a heteroatom-terminated compound, $CS_2$, and an olefin-containing compound.

Also disclosed herein are embodiments of a kit comprising a donor compound embodiment and further comprising water, a base, a buffer, a conversion component, such as a component that promotes or facilitates conversion of COS and/or $CS_2$ to $H_2S$, or any combination thereof. In some embodiments, the donor compound can be in a container separated from the water, the base, the buffer, and/or the conversion component and in some other embodiments, the donor compound can be in the same container as the conversion component. In some embodiments, the kit can include a separate container comprising the water, the base, or the buffer; or the base, water, and/or buffer can be provided by the user as a component separate from the kit. In some embodiments, the kit can further comprise a solubilizing agent, a filter, a multi-well plate, a test strip, a slide, a disc, or any combinations thereof.

Conversion components that can be included in the kit and/or the composition embodiments described above can be selected from, but are not limited to, any compound or species capable of converting COS and/or $CS_2$ to $H_2S$. In some embodiments, the conversion component can be carbonic anhydrase, nitrogenase, RuBisCO, CO dehydrogenase, COSase, $CS_2$ hydrolase, water, or any combinations thereof. The rate of $H_2S$ generation can also be modified by the amount of compound capable of converting COS and/or $CS_2$ to $H_2S$. In some embodiments, the conversion component is included in the kit in an amount ranging from 1 U/mL to 1000 U/mL, such as 1 U/mL to 500 U/mL, 1 U/mL to 250 U/mL, 1 U/mL to 100 U/mL, or 1 U/mL to 50 U/mL.

IV. Method of Making Donor Compound Embodiments

Also disclosed herein are embodiments of a method for making the donor compound embodiments. In some embodiments, the method comprises coupling starting material 100 with a coupling partner 102 or 104 to provide product 106, as illustrated in Scheme 1A. Another example of this coupling reaction is illustrated in Scheme 1B. With reference to Schemes 1A and 1B, the "LG" group of coupling partner 104 is a functional group that is displaced upon reaction with starting material 100. In some embodiments, the LG group can be a halogen, a sulfonic ester (e.g., mesylate, tosylate, besylate, or the like), or other such functional groups. In some embodiments, heat can be used to promote coupling between starting material 100 and coupling partner 102 or 104, and in yet some other embodiments, a base can be used to facilitate the coupling step (e.g., 1,8-Diazabicyclo[5.4.0]undec-7-ene or "DBU").

Scheme 1A

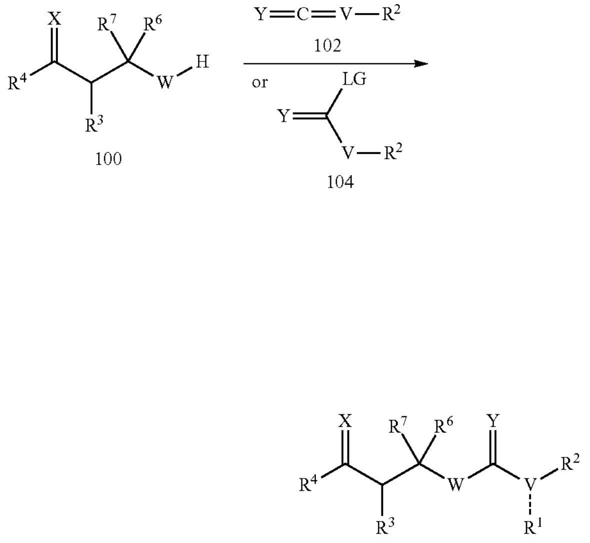
100
102
or
104
106

Scheme 1B
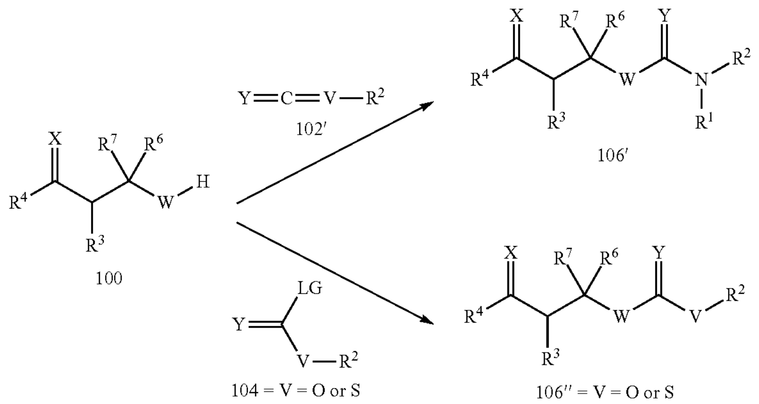
Additional method embodiments that can be used to make donor compound embodiments are illustrated below in Schemes 2-7. With reference to Schemes 2-7, each of X and W can be as recited in Formulas 1, 2A-2I, and 3A-3I, described above.
Scheme 2A
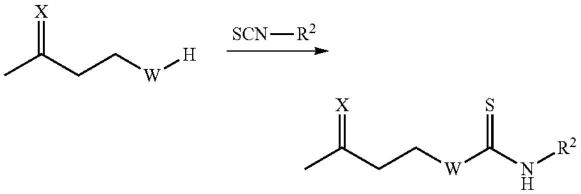
Scheme 2B
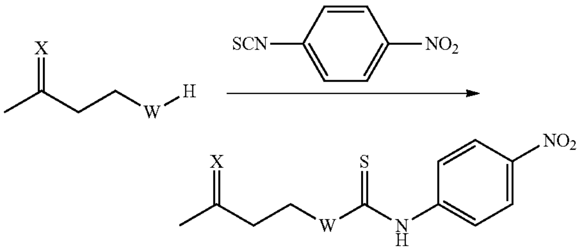
Scheme 3A
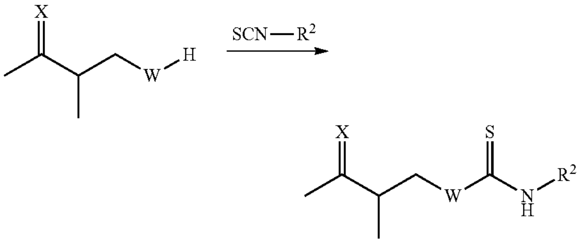
Scheme 3B
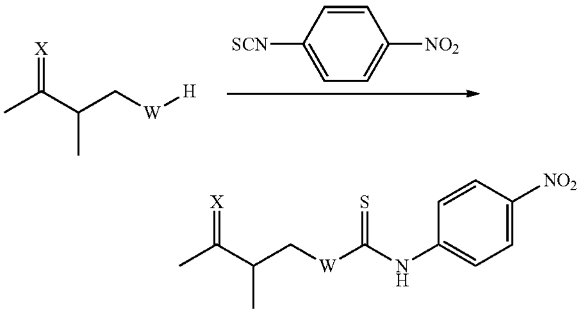
Scheme 4A
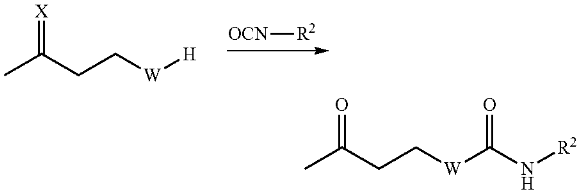
Scheme 4B
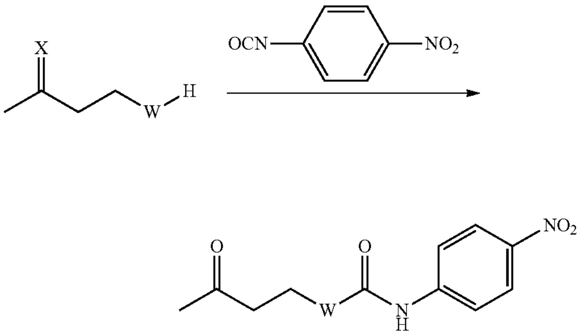

Scheme 5A

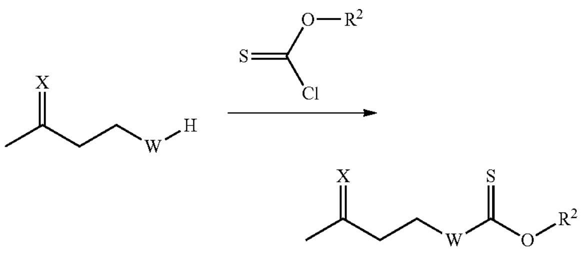

Scheme 5B

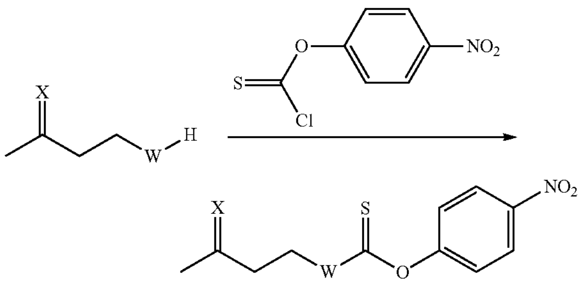

Scheme 6A

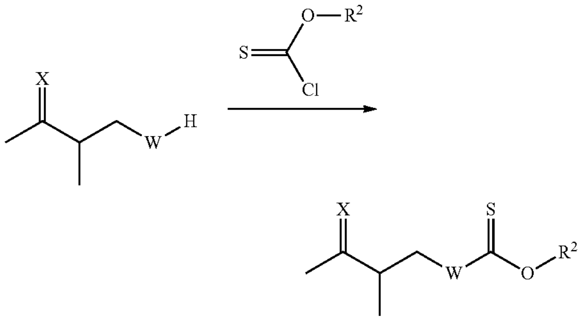

Scheme 6B

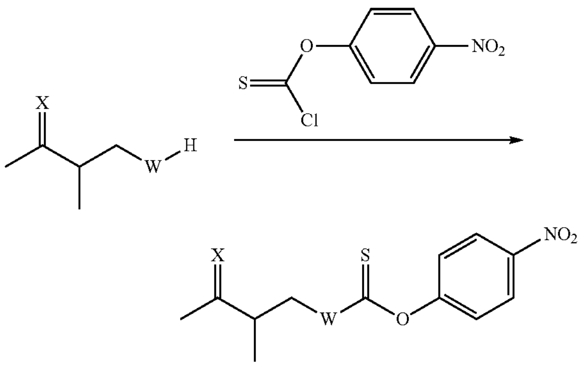

Scheme 7A

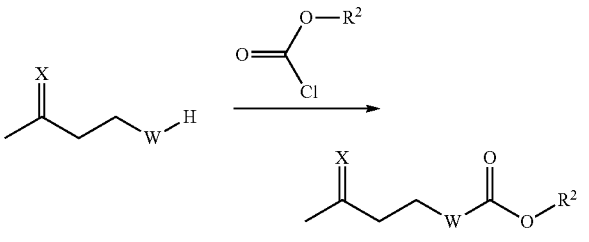

Scheme 7B

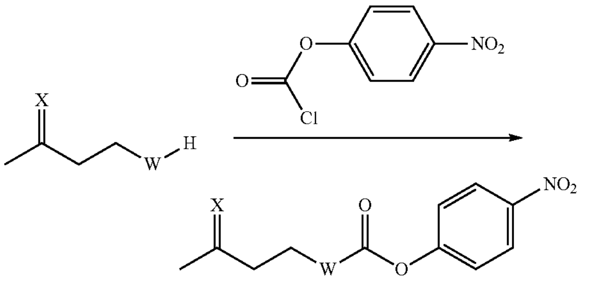

Representative method embodiments also are provided in the Examples section of the present disclosure.

V. Method of Using Donor Compound Embodiments

In embodiments described herein, the donor compound, or any composition thereof, can be used to generate $H_2S$ by way of releasing COS or $CS_2$ from the donor compound during a deprotonation and elimination reaction sequence. In additional embodiments, the donor compound can be used to deliver $H_2S$ (by way of releasing COS or $CS_2$) to a subject or sample in addition to delivering a therapeutic agent. As described in the formulas above, the donor compound can be coupled to a therapeutic agent. In such embodiments, the method described herein can facilitate release of this therapeutic agent from the donor compound, simultaneously (or substantially simultaneously) with COS or $CS_2$ release. The donor compound embodiments can be used in in vivo, in vitro, or ex vivo methods to increase $H_2S$ concentration and/or $H_2S$ activity in a sample or a subject and also to treat a subject by delivering a therapeutic agent to the subject.

In particular disclosed embodiments, method embodiments of using the donor compound embodiments can comprise exposing a subject or a sample to the donor compound or a composition thereof. In some embodiments, the method is an in vitro method and it comprises exposing a sample, such as a biological sample obtained from a subject (or other samples), to the donor compound or a composition thereof. In some embodiments, the method is an in vivo method and it comprises exposing a subject, such as a human or other animal, to the donor compound or a composition thereof (such as a pharmaceutical composition). In some embodiments, the subject or the sample can be exposed to an amount of the donor compound that is sufficient to increase the amount of $H_2S$ in the subject or sample to a certain level. For example, in subjects or samples that are determined to have deficient amounts of $H_2S$, the donor compound can be administered at a concentration sufficient to increase the $H_2S$ concentration back to a normally accepted level. What constitutes a "normally accepted level" can depend on the type of cell or tissue types involved, but could be determined by a person of ordinary skill in the art. In some embodiments, the "normally accepted level" can exist in the nanomolar to low micromolar range.

Dosage amounts, such as therapeutically effective amounts, of the donor compound embodiments typically are selected to be amounts that will deliver $H_2S$ and/or a therapeutic agent, wherein such compounds are individually delivered in amounts ranging from greater than 0 mg/kg/day (such as 0.0001 mg/kg/day, 0.001 mg/kg/day, or 0.01 mg/kg/day) to 100 mg/kg/day. In embodiments where the donor compound is administered as a pharmaceutical composition, the amount of the donor compound in the composition can be an amount sufficient to deliver $H_2S$ and/or a therapeutic agent (individually) in amounts ranging from greater than 0 mg/kg/day (such as 0.0001 mg/kg/day, 0.001 mg/kg/day, or 0.01 mg/kg/day) to 100 mg/kg/day.

In some embodiments, the method can further comprise exposing the subject or the sample to a component that facilitates deprotonation of the donor compound thereby facilitating elimination of COS or $CS_2$ (or any combination thereof, such as in embodiments where two different donor compounds are used). Without intending to be limited to a particular theory, it is currently believed that the donor compound will be deprotonated either by way of being combined with an aqueous buffer, a naturally occurring basic compound (present in the sample or the subject), or a suitable exogenous base. In some embodiments, the subject or the sample may not require exposure to an exogenous source of this component as the subject or sample may inherently comprise a component that can facilitate deprotonation of the donor compound. In embodiments where this component is added to the subject or the sample, it can be administered by any suitable means (e.g., immersing the sample in a solution comprising the component; or by oral administration, parenteral administration, or the like). The deprotonation step typically generates an olefin-containing intermediate (which need not be an intermediate capable of isolation) that then eliminates (or releases) COS or $CS_2$. In some embodiments, the deprotonation step and the elimination step can occur simultaneously or substantially simultaneously. In yet some additional embodiments, the deprotonation step and the elimination step can occur sequentially.

In some embodiments, the method can further comprise exposing the subject or the sample to a conversion component that is capable of converting COS and/or $CS_2$ to $H_2S$. In some embodiments, the conversion component can be naturally occurring in the subject or the sample and therefore a separate administration step is not need. In other embodiments, the subject or the sample can be administered a conversion component that facilitates $H_2S$ production. Suitable conversion components are described above. In some particular embodiments, the conversion component is water, carbonic anhydrase, or any combination thereof. In some additional embodiments, the conversion component is nitrogenase, RuBisCO, CO dehydrogenase, COSase, $CS_2$ hydrolase, water, or any combination thereof.

In some embodiments, the method can further comprise detecting and/or measuring a detectable signal produced after exposing the sample or the subject to the donor compound, or after exposing the sample or the subject to a component that facilitates deprotonation of the donor compound (either before or after the subject or sample has been exposed to the donor compound). In some embodiments, the detectable signal is produced by release of a heteroatom-terminated compound from the donor compound. Solely by way of example, in some embodiments, the donor compound can release a p-nitroaniline group, which provides a colorimetric signal that can be readily detected by the plain eye. In such an exemplary embodiment, because a colorimetric signal is produced when COS and/or $CS_2$ is released, the donor compound provides a means by which to visually detect $H_2S$ release. Such embodiments are useful for diagnostic methods and/or analytical methods using a biological sample or that are used in a subject. In some embodiments, detecting a detectable signal can comprise visualizing a color change in a sample (e.g., by using the naked eye). In some embodiments, measuring a detectable signal can comprise using a measurement technique, such as using spectroscopic methods (e.g., UV-visible spectroscopy, fluorescence spectroscopy, phosphorescence spectroscopy, or the like). A representative chemical scheme illustrating detectable signal production is illustrated in Scheme 8.

Scheme 8

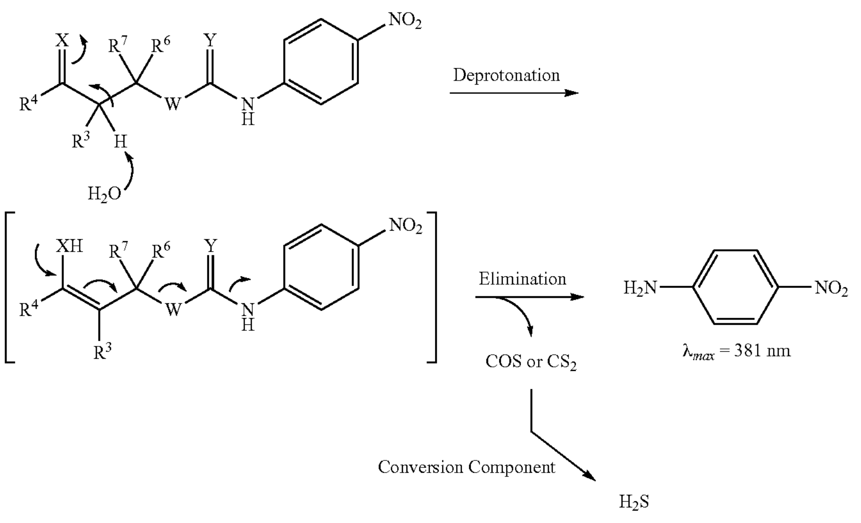

In some embodiments, a control compound can be used as a comparative tool in detecting or measuring a detectable signal produced by a donor compound and/or composition described herein, such as to provide a baseline for the detection or measurement and/or for evaluating a donor compound's ability to produce the detectable signal, COS, and/or $CS_2$. For example, compounds lacking one or more hydrogen atoms adjacent to a "C═X" functional group (as illustrated in Formula 1) would not undergo deprotonation, therefore, leading to no $COS/H_2S$ release, such as is illustrated in Scheme 9 (wherein $R^8$ is not hydrogen). Other compounds, such as the compound illustrated in Scheme 10, would release $CO_2$ instead of COS or $CS_2$, resulting in no $H_2S$ production. As such, these comparative compounds can be used to elucidate the $COS/H_2S$-related effects of donor compounds of the present disclosure.

Scheme 9

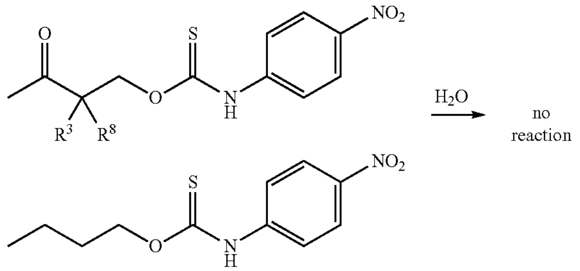

Scheme 10

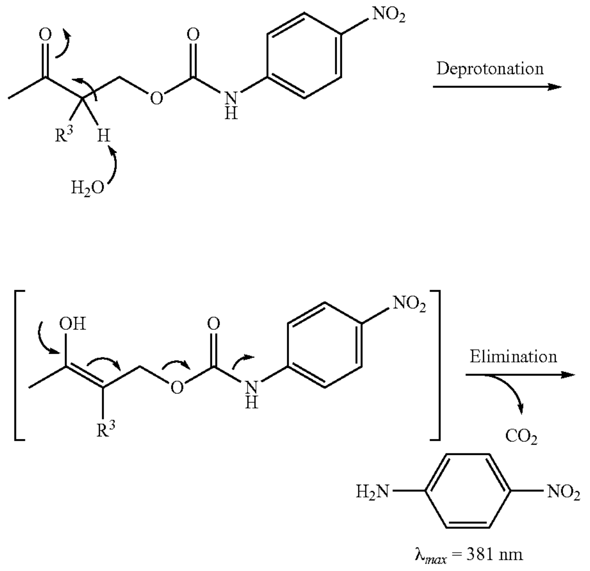

A representative compound γ-KetoTCM-3 and n-butylthiocarbamate (n-BuTCM-1), which are triggerless control compounds that do not release $COS/H_2S$ (see Scheme 9A) can be used, as well as a representative γ-ketocarbamate molecule, γ-KetoCM-1, which releases $CO_2$ instead of COS (Scheme 10A).

Scheme 9A

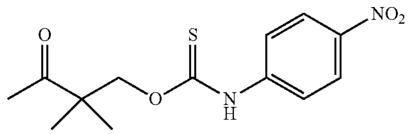

g-KetoTCM-3 and

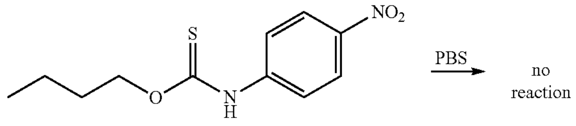

n-BuTCM-1

Scheme 10A

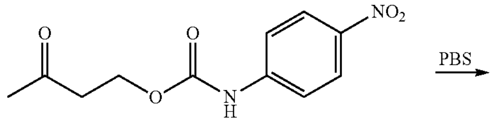

g-KetoCM-1

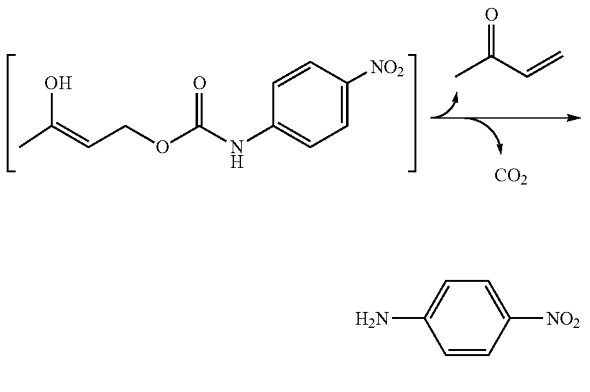

In some embodiments, the donor compound can be used to deliver a combination of $H_2S$ and a therapeutic agent to a subject or sample. In such embodiments, the donor compound typically is coupled to the therapeutic agent such that when deprotonation and elimination occur, the therapeutic agent (or a precursor thereto) is released with COS or $CS_2$. Such a method is described by Scheme 11 below, with a representative example illustrated in Scheme 12. While a representative example of such an embodiment is illustrated below in Scheme 12, the present disclosure is not limited to this particular example and a person of ordinary skill in the art would understand that other therapeutic agents could be coupled to the donor compound embodiments described herein and would recognize, with the benefit of the present disclosure, how such therapeutic agents can be coupled to the donor compound embodiments.

Scheme 11

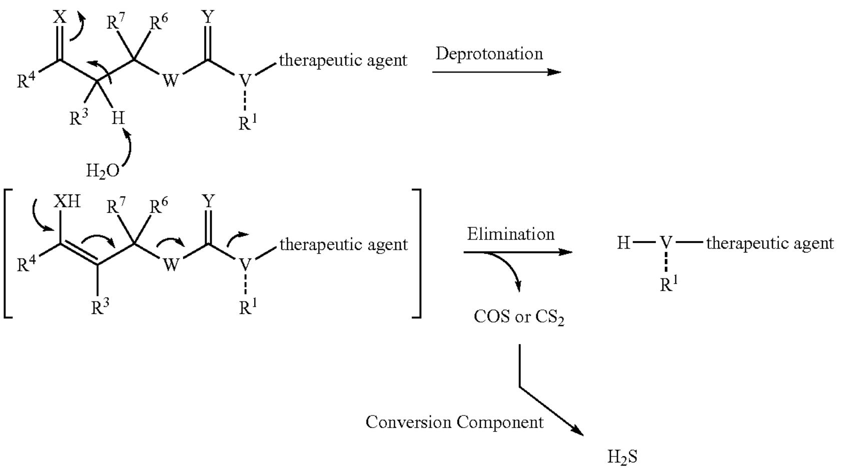

Scheme 12

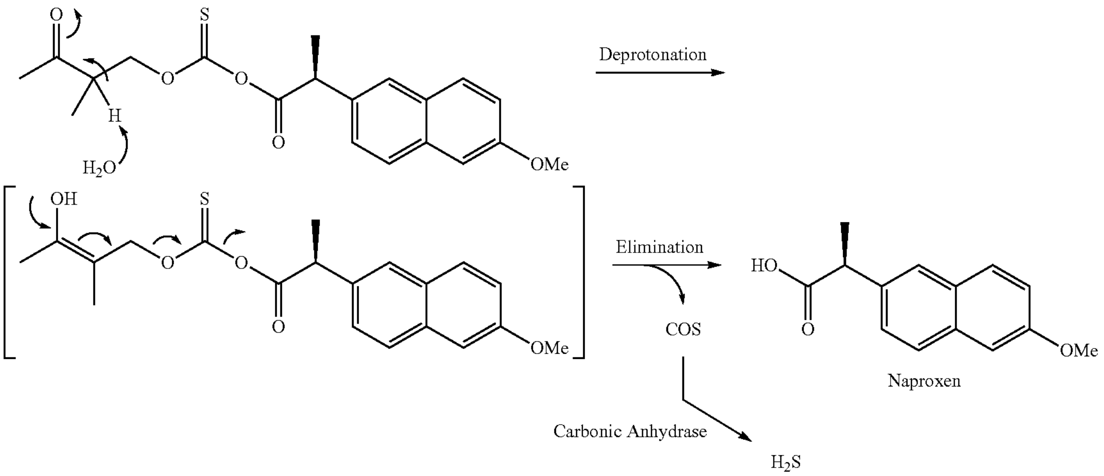

In some embodiments, the method can further comprise controlling the rate of COS and/or $CS_2$ release (and thus $H_2S$ release) from the donor compound embodiments by modifying the pH of the environment surrounding the donor compound embodiment. For example, in in vitro method embodiments, the pH of the sample (or the environment of the sample, such as when the sample is in solution) can be modified to be higher than or lower than physiological pH, which typically is pH 7.4. In some embodiments, the pH of the sample (or the environment of the sample, such as when the sample is in solution) can be modified by using a buffer having a pH higher than 7.4, such as 7.5 or higher (e.g., pH 8). In particular disclosed embodiments, modifying the pH of the sample in this manner will increase the rate of COS/$H_2S$ release. In some other embodiments, the pH of the sample can be modified by using a buffer having a pH lower than 7.4, such as pH 7.3 or lower (e.g., pH 6). In particular disclosed embodiments, modifying the pH of the sample in this manner will decrease the rate of COS/$H_2S$ release.

VI. Overview of Several Embodiments

Disclosed herein are embodiments of a donor compound that have a structure satisfying Formula I Formula 1

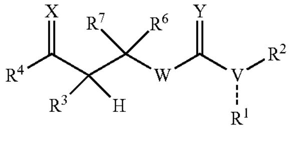

wherein

X is oxygen, sulfur, NR' or $N^+(R')_2$, wherein each R' independently is hydrogen, aliphatic, haloaliphatic, haloheteroaliphatic, heteroaliphatic, aromatic, or any combination thereof;

W is oxygen or sulfur;

Y is oxygen when W is sulfur or Y is sulfur when W is oxygen or when W is sulfur;

V is a heteroatom;

$R^1$, if present, is hydrogen, aliphatic, haloaliphatic, haloheteroaliphatic, heteroaliphatic, aromatic, or any combination thereof;

$R^2$ is aliphatic, aromatic, heteroaliphatic, or $R^1$ and $R^2$ when taken together with V is a heteroaliphatic group;

$R^3$ is hydrogen, halogen, aliphatic, haloaliphatic, haloheteroaliphatic, heteroaliphatic, aromatic, or any combination thereof;

$R^4$ is hydrogen, halogen, aliphatic, haloaliphatic, haloheteroaliphatic, heteroaliphatic, aromatic, or any combination thereof; and each of $R^6$ and $R^7$ independently is hydrogen, aliphatic, haloaliphatic, haloheteroaliphatic, heteroaliphatic, aromatic, or any combination thereof.

In some embodiments, the donor compound has a structure satisfying one or more of Formulas 2A-2I:

Formula 2A

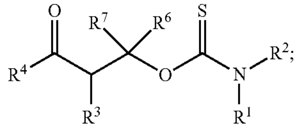

Formula 2B

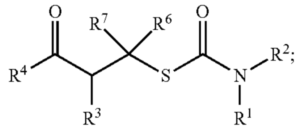

Formula 2C

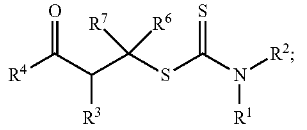

Formula 2D

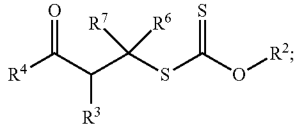

Formula 2E

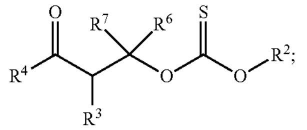

Formula 2F

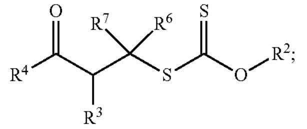

Formula 2G

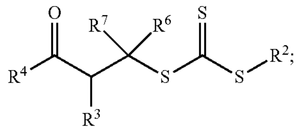

Formula 2H

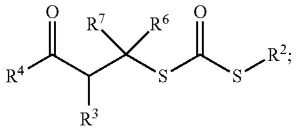 or

-continued

Formula 2I

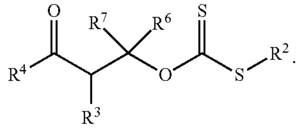

In any or all of the above embodiments, $R^2$ further comprises a therapeutic agent.

In any or all of the above embodiments, X is oxygen, sulfur, or NR' or $N^+(R')_2$, wherein each R' independently is hydrogen, alkyl, alkenyl, akynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-aryl/alkenyl-aryl/alkynyl-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryt/heteroalkynyl-heteroaryl or any combination thereof.

In any or all of the above embodiments, V is oxygen, sulfur, or nitrogen.

In any or all of the above embodiments, $R^1$ is present and is hydrogen, alkyl, alkenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alky-aryl/alkenyl-aryl/alkynyl-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkyny-heteroaryl, or any combination thereof.

In any or all of the above embodiments, $R^2$ is aromatic; -aromatic-$(R^5)_m$, wherein m is an integer selected from 0-5 and each $R^5$ independently is an electron-donating group, an electron-withdrawing group, a therapeutic agent; alkyl, alkenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-aryl/alkenyl-aryl/alkyny-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkyny-heteroaryl, or any combination thereof.

In any or all of the above embodiments, $R^3$ is hydrogen, C, Br, F, I, alkyl, alkenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alky-aryl/alkenyl-aryl/alkynyl-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkyny-heteroaryl, or any combination thereof.

In any or all of the above embodiments, $R^4$ is hydrogen, C, Br, F, I, alkyl, alkenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alky-aryl/alkenyl-aryl/alkynyl-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkyny-heteroaryl, or any combination thereof.

In any or all of the above embodiments, $R_6$ and $R^7$ independently are hydrogen, C, Br, F, I, alkyl, alkenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-aryl/ alkenyl-aryl/alkynyl-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkyny-heteroaryl, or any combination thereof.

In any or all of the above embodiments, X is oxygen or sulfur.

In any or all of the above embodiments, $R^1$ is present and is hydrogen or lower alkyl.

In any or all of the above embodiments, $R^2$ is aryl; heteroaryl; -aliphatic-aryl; -aliphatic-heteroaryl; -heteroaliphatic-aryl; -heteroaliphatic-heteroaryl; or -aliphatic-aryl-$(R^5)_m$, -aliphatic-heteroaryl-$(R^5)_m$, -heteroaliphatic-aryl-$(R^5)_m$, -heteroaliphatic-heteroaryl-$(R^5)_m$, -aryl-$(R^5)_m$ or -heteroaryl-$(R^5)_m$ wherein m is an integer selected from 0-5 and each $R^5$ independently is aldehyde, ketone, ester (—$COOR^a$ or —$OCOR^a$), carboxylic acid, acyl, acyl halide, cyano, sulfonate, nitro, nitroso, pyridinyl, alkyl halide, halogen (e.g., chloro, bromo, fluoro, or iodo), haloaliphatic, ammonium, amide (—$CONH_2$ or —$NHCOR^a$), alkoxy, thioether, amine (e.g., primary, secondary, tertiary, or quaternary amine), hydroxyl, thiol, ether, acyloxy, aliphatic (e.g., alkyl, alkenyl, alkyny), aryl, aliphatic-aryl, heteroaliphatic-aryl, an NSAID or other therapeutic agent, or any combinations thereof.

In any or all of the above embodiments, $R^3$ is hydrogen or lower alkyl.

In any or all of the above embodiments, $R^4$ is lower alkyl or an ester.

In any or all of the above embodiments, $R_6$ and $R^7$ are hydrogen.

In some embodiments, $R^2$ and $R^1$ together with V form a 4-, 5-, 6-, or 7-membered heterocyclic group.

In some embodiments, $R^2$ comprises 4-methy-2H-chromen-2-one, 2-(2-methoxyethyl)-1H-benzo[de]isoquinoline-1,3(2H)-dione, or methylrhodol.

In some embodiments, the donor compound has a structure satisfying any one or more of Formulas 3A-3I:

Formula 3A

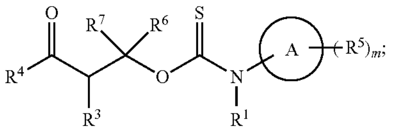

Formula 3B

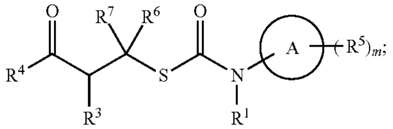

Formula 3C

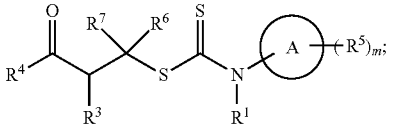

Formula 3D

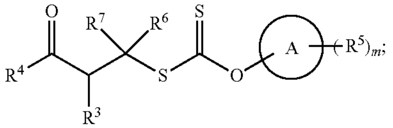

-continued

Formula 3E

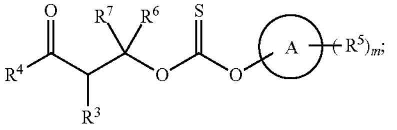

Formula 3F

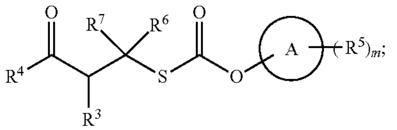

Formula 3G

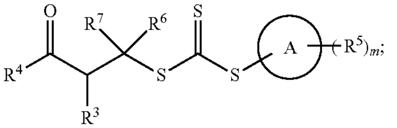

Formula 2H

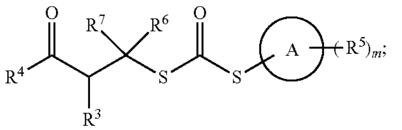

or

Formula 2I

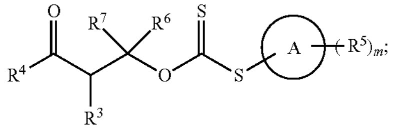

wherein m is an integer selected from 0-5 and each $R^5$ independently is an electron-donating group, an electron-withdrawing group, a therapeutic agent, aliphatic, heteroaliphatic, or any combination thereof; and ring A is an aromatic group, an aliphatic-aromatic group, or a heteroaliphatic-aromatic group.

Also disclosed herein is a pharmaceutical composition, comprising a compound according to any or all of the above embodiments, and an additional compositional component selected from a pharmaceutically acceptable excipient, water, a buffer, a conversion component, or two or more thereof.

Also disclosed herein are embodiments of a composition, comprising two or more of:

a heteroatom-terminated compound;

COS, $CS_2$, $H_2S$, or any combination thereof; or an olefin-containing compound having a structure satisfying Formula 4

Formula 4

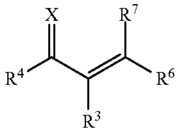

wherein

X is oxygen, sulfur, NR' or $N^+(R')_2$, wherein each R' independently is hydrogen, aliphatic, haloaliphatic, haloheteroaliphatic, heteroaliphatic, aromatic, or any combination thereof;

$R^3$ is hydrogen, halogen, aliphatic, haloaliphatic, haloheteroaliphatic, heteroaliphatic, aromatic, or any combination thereof;

$R^4$ is hydrogen, halogen, aliphatic, haloaliphatic, haloheteroaliphatic, heteroaliphatic, aromatic, or any combination thereof; and each of $R^6$ and $R^7$ independently is hydrogen, aliphatic, haloaliphatic, haloheteroaliphatic, heteroaliphatic, aromatic, or any combination thereof.

In some embodiments, the composition comprises the heteroatom-terminated compound and COS, $CS_2$, $H_2S$, or any combination thereof.

In any or all of the above embodiments, the composition comprises the olefin-containing compound and COS, $CS_2$, $H_2S$, or any combination thereof.

In any or all of the above embodiments, the composition comprises the olefin-containing compound and the heteroatom-terminated compound.

Also disclosed herein are embodiments of a method, comprising exposing a sample or a subject to a compound according to any or all of the above embodiments, or a pharmaceutical composition according to embodiments described above.

In some embodiments, the method further comprises exposing the sample or the subject to carbonic anhydrase, nitrogenase, RuBisCO, CO dehydrogenase, COSase, $CS_2$ hydrolase, water, or any combination thereof.

In any or all of the above embodiments, the method can further comprise analyzing the sample or the subject to detect a reaction of the compound that produces a detectable signal, COS, $CS_2$, $H_2S$, or any combination thereof. In some embodiments, analyzing comprises observing or detecting a color change, a fluorescence change, or a change in concentration of COS, $CS_2$, $H_2S$ or any combination thereof.

In any or all of the above embodiments, the method can further comprise measuring an amount of COS, $CS_2$, or $H_2S$ released from the compound.

In any or all of the above embodiments, the sample is a biological sample selected from a cell, tissue, and/or bodily fluid.

In some embodiments, the method comprises exposing a subject that has or is at risk of developing a disease associated with $H_2S$ deficiency or $H_2S$ misregulation and/or a disease associated with carbonic anhydrase overexpression.

In some embodiments, the disease is a cardiovascular disease, diabetes, inflammation, a neurological disease, cancer, a disease involving insufficient wound healing, erectile dysfunction, or any combinations thereof.

In some embodiments, the cardiovascular disease is heart failure, myocardial reperfusion injury, atherosclerosis, hypertension, hypertrophy, or any combinations thereof.

Also disclosed herein are embodiments of a kit, comprising:

a compound according to any or all of the above compound embodiments; and a filter, a multi-well plate, a test strip, a slide, a disc, a container, an enzyme, carbonic anhydrase, nitrogenase, RuBisCO, CO dehydrogenase, COSase, $CS_2$ hydrolase, water, a solubilizing agent, or any combination thereof.

VII. Examples

Methods and Materials—Reagents were purchased from Sigma-Aldrich, Tokyo Chemical Industry (TCI), Fisher Scientific, Combi-Blocks, and VWR and used directly as received. Silica gel (SiliaFlash F60, Silicycle, 230-400 mesh) was used for column chromatography. Deuterated solvents were purchased from Cambridge Isotope Laboratories (Tewksbury, Mass., USA). $^1H$ and $^{13}C$ {$^1H$} NMR spectra were recorded on Bruker 500 MHz or Bruker 600 MHz NMR instruments at the indicated frequencies. Chemical shifts are reported in ppm relative to residual protic solvent resonances. Mass spectrometric measurements were performed by the University of Illinois, Urbana Champaign MS facility, or on a Xevo Waters ESI LC/MS instrument. PNA formation and methylene blue absorbance were monitored by using Agilent Cary 100 or Cary 60 UV-Vis spectrometers. NaSH (99% purity) was purchased from Strem Chemicals, Inc. SF7-AM was synthesized by following the literature report. HeLa cells and RAW 264.7 cells were purchased from ATCC (Manassas, Va., USA). Cell imaging experiments were performed on a Leica DMi8 fluorescence microscope, equipped with an Andor Zyla 4.2+ sCMOS detector. $NO_2^-$ levels were obtained by using a Griess Reagent kit (Thermo Fisher Scientific) and the absorbance at 548 nm was measured by using a microplate reader (Tecan Spark 20M)

Example 1

In this example, two donor compounds (compounds γ-KetoTCM-1 and γ-KetoTCM-2) were made, along with three comparative compounds (γ-KetoTCM-3 and n-BuTCM-1, and γ-KetoCM-1) were made. In this example, a suitable alcohol starting material was reacted with p-nitrophenyl isothiocyanate or isocyanate as illustrated in Schemes 13-17.

Scheme 13

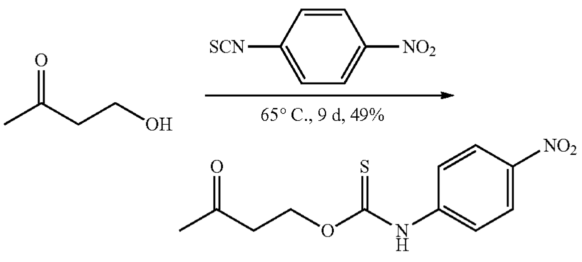

γ-KetoTCM-1

γ-KetoTCM-1: 4-Hydroxy-2-butanone (880 mg, 10.0 mmol) was combined with p-nitrophenyl isothiocyanate (180 mg, 1.00 mmol) in anhydrous THF (10.0 mL). The reaction mixture was stirred at room temperature for 3 days. The reaction was then quenched by adding brine (25 mL), and the aqueous solution was extracted with ethyl acetate (3×15 mL). The organic layers were combined, dried over $MgSO_4$, and evaporated under vacuum. γ-KetoTCM-1 was isolated as yellow solid (91.5 mg, 34% yield) after purification by column chromatography using ethyl acetate/hexanes (1/1, v/v, $R_f$=0.41) as the eluent. $^1H$ NMR (500 MHz, DMSO-$d_6$) δ (ppm): 11.64 (s, 1H, NH), 8.22 (d, J=10.0 Hz, 2H, aryl H), 7.77 (br, 2H, aryl H), 4.66 (t, J=5.0 Hz, 2H, $CH_2O$), 3.02 (t, J=5.0 Hz, 2H, $CH_2$), 2.17 (s, 3H, $CH_3$). $^{13}C$ {$^1H$} NMR (150 MHz, DMSO-$d_6$) δ (ppm): 206.5 (C═O), 188.0 (C═S), 143.5 (aryl C), 125.1 (aryl C), 121.6 (aryl C), 112.8 (aryl C), 66.6 ($CH_2O$), 41.7 ($CH_2$), 30.5 ($CH_3$). IR ($cm^{-1}$): 3248, 3081, 1722, 1599, 1552, 1493, 1393, 1366, 1331, 1164, 1113, 1048, 842. HRMS m/z $[M+Na]^+$ calcd. For $[C_{11}H_{12}N_2NaO_4S]^+$ 291.0415; found 291.0417. Elemental analysis (calculated value for $C_{11}H_{12}N_2O_4S$): C, 49.51 (49.24); H, 4.65 (4.51); N, 10.39 (10.44); S, 11.52 (11.95).

Scheme 14

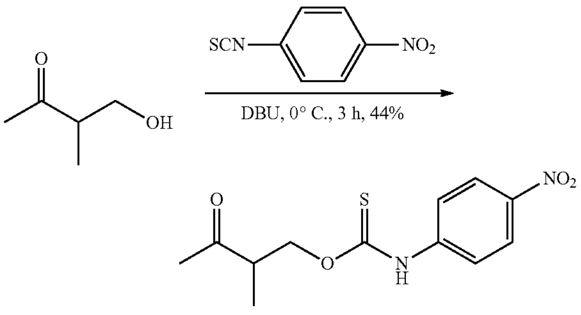

γ-KetoTCM-2

γ-KetoTCM-2: This compound was prepared by reacting 4-hydroxy-3-methy-2-butanone (102 mg, 1.00 mmol) with p-nitrophenyl isothiocyanate (180 mg, 1.00 mmol) in anhydrous THF (10.0 mL) and cooled to 0° C. DBU (152 mg, 1.00 mmol) was then added, and the reaction solution was stirred at room temperature until the completion of the reaction indicated by TLC. The reaction was then quenched by adding brine (25 mL), and the aqueous solution was extracted with ethyl acetate (3×15 mL). The organic layers were combined, dried over $MgSO_4$, and evaporated under vacuum. γ-KetoTCM-2 was purified by column chromatography using ethyl acetate/hexanes (1/1, v/v, $R_f$=0.50) as the eluent (123 mg, 44% yield). $^1H$ NMR (500 MHz, DMSO-8) δ (ppm): 11.65 (s, 1H, NH), 8.22 (d, J=10.0 Hz, 2H, aryl H), 7.76 (br, 2H, aryl H), 4.60 (m, 2H, $CH_2O$), 3.13 (m, 1H, CH), 2.51 (s, 3H, $CH_3$), 1.14 (d, J=5.0 Hz, 3H, $CH_3$). $^{13}C$ {$^1H$} NMR (125 MHz, DMSO-$d_6$) δ (ppm): 209.7 (C═O), 187.9 (C═S), 143.6 (aryl C), 125.1 (aryl C), 121.8 (aryl C), 72.3 ($CH_2O$), 45.5 (CH), 28.9 ($CH_3$), 13.5 ($CH_3$). IR ($cm^{-1}$): 3276, 3092, 1703, 1597, 1557, 1505, 1362, 1318, 1304, 1172, 1137, 1026, 849. HRMS m/z $[M+H]^+$ calcd. For $[C_{12}H_{15}N_2O_4S]^+$ 283.0783; found 283.0753. Elemental analysis (calculated value for $C_{12}H_{14}N_2O_4S$): C, 51.20 (51.05); H, 5.06 (5.00); N, 9.77 (9.92); S, 11.26 (11.36).

Scheme 15

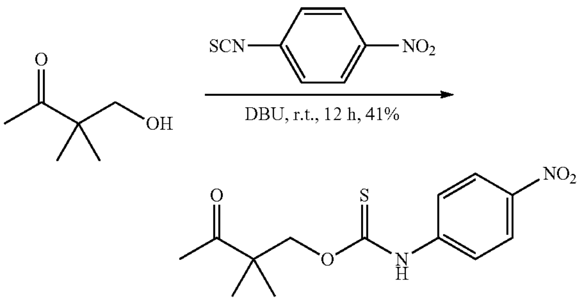

γ-KetoTCM-3

γ-KetoTCM-3: This compound was prepared by reacting 4-hydroxy-3,3-dimethyl-2-butanone (116 mg, 1.00 mmol) with p-nitrophenyl isothiocyanate (180 mg, 1.00 mmol) in anhydrous THF (10.0 mL) and cooled to 0° C. DBU (152 mg, 1.00 mmol) was then added, and the reaction solution was stirred at room temperature until the completion of the reaction indicated by TLC. The reaction was then quenched by adding brine (25 mL), and the aqueous solution was extracted with ethyl acetate (3×15 mL). The organic layers were combined, dried over $MgSO_4$, and evaporated under vacuum. γ-KetoTCM-3 was purified by column chromatography using ethyl acetate/hexanes (1/1, v/v, $R_f$=0.64) as the eluent (121 mg, 41% yield). $^1H$ NMR (500 MHz, DMSO-$d_6$) δ (ppm): 11.62 (s, 1H, NH), 8.23 (d, J=10.0 Hz, 2H, aryl H), 7.72 (br, 2H, aryl H), 4.53 (s, 2H, $CH_2O$), 2.18 (s, 3H, $CH_3$), 1.19 (s, 6H, $2CH_3$). $^{13}C$ {$^1H$} NMR (125 MHz, DMSO-$d_6$) δ (ppm): 211.4 (C═O), 187.9 (C═S), 143.6 (aryl C), 125.0 (aryl C), 121.9 (aryl C), 47.8 ($CH_2O$), 25.8 ($CH_3$), 21.8 ($CH_3$). IR ($cm^{-1}$): 3247, 3218, 3058, 1686, 1598, 1568, 1508, 1498, 1422, 1365, 1321, 1304, 1164, 1136, 1111, 1038, 848. HRMS m/z $[M+H]^+$ calcd. For $[C_{13}H_{17}N_2O_4S]^+$ 297.0909; found 297.0922. Elemental analysis (calculated value for $C_{13}H_{16}N_2O_4S.H_2O$): C, 49.81 (49.67); H, 5.67 (5.77); N, 9.53 (8.91); S, 10.34 (10.20).

Scheme 16

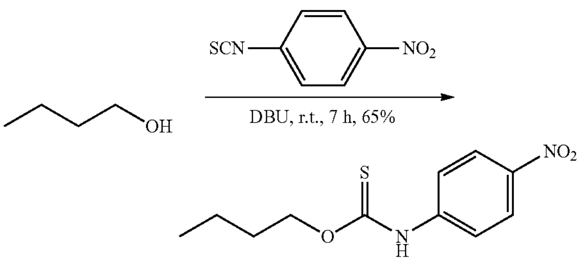

n-BuTCM-3 n-BuTCM-1: This compound was prepared by reacting n-butanol (74.0 mg, 1.00 mmol) with p-nitrophenyl isothiocyanate (180 mg, 1.00 mmol) in anhydrous THF (10.0 mL) and cooled to 0° C. DBU (152 mg, 1.00 mmol) was then added, and the reaction solution was stirred at room temperature until the completion of the reaction indicated by TLC. The reaction was then quenched by adding brine (25 mL), and the aqueous solution was extracted with ethyl acetate (3×15 mL). The organic layers were combined, dried over $MgSO_4$, and evaporated under vacuum. n-BuTCM-1 was purified by column chromatography using ethyl acetate/hexanes (1/3, v/v, $R_f$=0.64) as the eluent (166 mg, 65% yield). $^1H$ NMR (500 MHz, DMSO-de) δ (ppm): 11.61 (s, 1H, NH), 8.24 (d, J=10.0 Hz, 2H, aryl H), 7.82 (br, 2H, aryl H)), 4.52 (t, J=5.0 Hz, 2H, $CH_2O$), 1.75 (quintet, J=5.0 Hz, 2H, $CH_2$), 1.40 (sextet, J=5.0 Hz, 2H, $CH_2$), 0.93 (t, J=5.0 Hz, 3H, $CH_3$). $^{13}C$ {$^1H$} NMR (125 MHz, DMSO-de) δ (ppm): 188.3 (C═S), 144.5 (aryl C), 143.4 (aryl C), 125.1 (aryl C), 121.6 (aryl C), 71.4 ($CH_2O$), 30.4 ($CH_2$), 19.1 ($CH_2$), 14.1 ($CH_3$). IR ($cm^{-1}$): 3242, 2965, 2934, 1609, 1596, 1552, 1508, 1493, 1398, 1324, 1305, 1194, 1113, 1060, 1024, 844. HRMS m/z $[M+H]^+$ calcd. For $[C_{11}H_{15}N_2O_3S]^+$ 255.0803; found 255.0814. Elemental analysis (calculated value for $C_{11}H_{14}N_2O_3S$): C, 52.25 (51.95); H, 5.70 (5.55); N, 10.96 (11.02); S, 12.23 (12.61). DBU (152 mg, 1.0 mmol).

Scheme 17

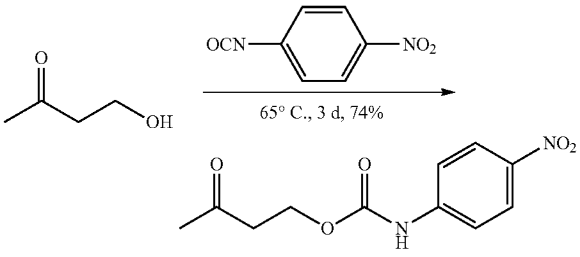

γ-KetoCM-1

γ-KetoCM-1: 4-Hydroxy-2-butanone (88.0 mg, 1.00 mmol) was combined with p-nitrophenyl isocyanate (240 mg, 1.50 mmol) in anhydrous THF (10.0 mL). The reaction mixture was refluxed at 65° C. for 3 days. The reaction was cooled to room temperature and then quenched by adding brine (25 mL) and the aqueous solution was extracted with ethyl acetate (3×15 mL). The organic layers were combined, dried over $MgSO_4$, and evaporated under vacuum. γ-KetoCM-1 was isolated as yellow solid (187 mg, 74% yield) after purification by column chromatography using ethyl acetate/hexanes (1/1, v/v, $R_f$=0.28) as the eluent. $^1H$ NMR (500 MHz, DMSO-$d_6$) δ (ppm): 10.38 (s, 1H, NH), 8.21 (d, J=10.0 Hz, 2H, aryl H), 7.70 (d, J=5.0 Hz, 2H, aryl H), 4.33 (t, J=5.0 Hz, 2H, $CH_2O$), 2.88 (t, J=5.0 Hz, 2H, $CH_2$), 2.16 (s, 3H, $CH_3$). $^{13}C$ {$^1H$} NMR (125 MHz, DMSO-$d_6$) δ (ppm): 206.5 (C═O), 153.6 (C(O)NH), 146.1 (aryl C), 142.1 (aryl C), 125.5 (aryl C), 118.1 (aryl C), 60.5 ($CH_2O$), 42.3 ($CH_2$), 30.4 ($CH_3$). IR ($cm^{-1}$): 3348, 3133, 1727, 1701, 1613, 1598, 1545, 1507, 1411, 1327, 1306, 1217, 1180, 1118, 1061, 854, 751. HRMS m/z $[M+Na]^+$ calcd. For $[CH_{12}N_2NaO_5]^+$ 275.0644; found 275.0644. Elemental analysis (calculated value for $CH_{12}N_2O_5$): C, 52.41 (52.38); H, 4.88 (4.80); N, 11.16 (11.11).

Example 2

To investigate COS/$H_2S$ release from donor compound embodiments, γ-KetoTCM-1 (50 μM) was incubated in PBS (pH 7.4, 10 mM) containing CA (25 μg/mL) and $H_2S$ release was detected by monitoring para-nitroaniline (PNA) formation at 37° C. In particular, a γ-KetoTCM-1 stock solution (15.0 μL, 10.0 mM in DMSO) was added to 3.00 mL of PBS (pH 6.00, 7.40 or 8.00, 10.0 mM) containing CA (25.0 μg/mL) in a quartz UV cuvette. The absorbance (250-500 nm) was measured and recorded by using Agilent Cary 100 or Cary 60 UV-Vis spectrometers at 37° C. k. was then obtained by plotting the absorbance ratio of PNA and γ-KetoTCM-1 versus time and $t_{1/2}$ was calculated by dividing In(2) by $k_{obs}$.

Figure 1B:
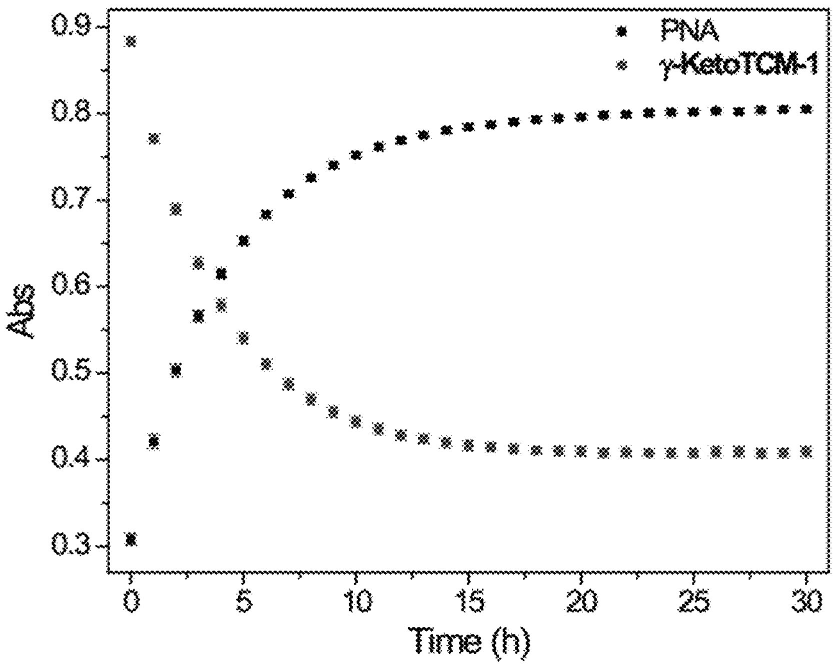
FIG. 1B is a graph of absorbance of a function of time (hours) showing p-nitroaniline formation and compound consumption of γ-KetoTCM-1 as monitored by UV-Vis spectroscopy.
Figure 1C:
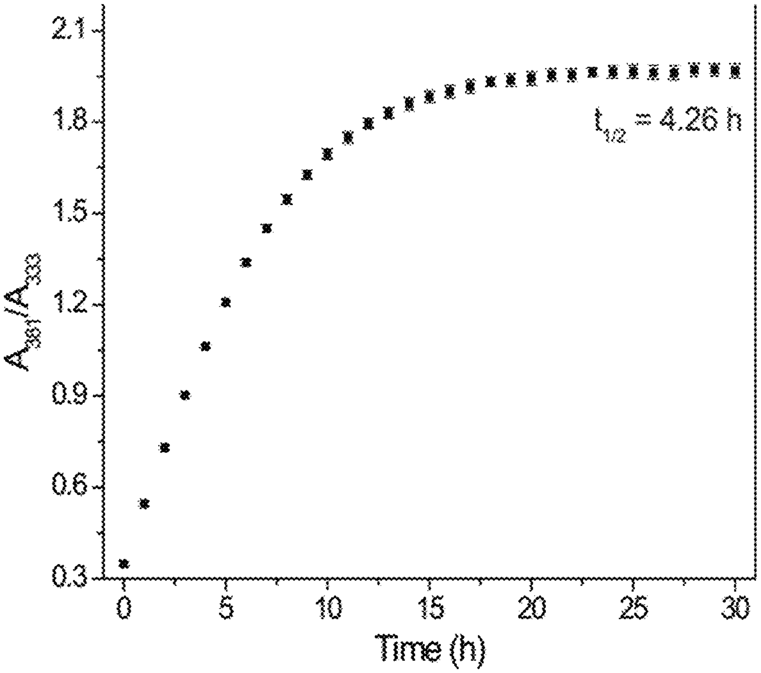

UV-Vis measurement indicated PNA formation as the absorbance at 381 nm increased. Meanwhile, γ-KetoTCM-1 consumption was observed as the absorbance at 333 nm decreased (FIGS. 1A and 1B). These results demonstrate that γ-KetoTCM-1 is labile and releases $H_2S$ in PBS containing CA. The kinetic study suggests that COS/$H_2S$ releasing rate at pH 7.4 is moderate with a half-life time ($t_{1/2}$) of 4.26 hours at 37° C. (FIG. 1C).

Figure 2:
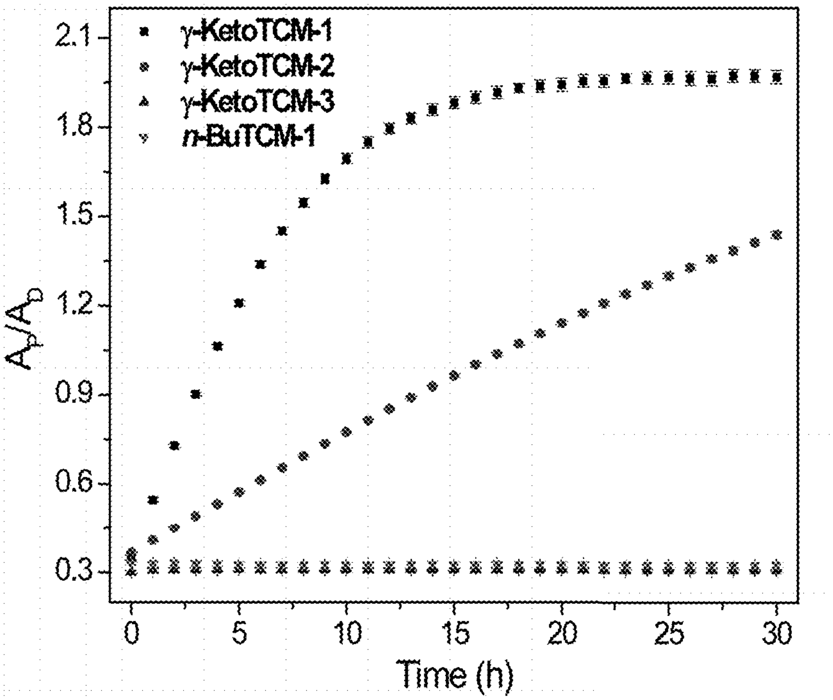
FIG. 2 is a graph showing results obtained from measuring PNA formation after compound activation, wherein $A_P$: PNA absorbance (381 nm); and $A_D$: compound absorbance (at $\lambda_{max}$).

Next, COS/$H_2S$ release from other donor molecules was evaluated. Although the similar treatment of γ-KetoTCM-2 led to COS/$H_2S$ release, such release was much slower compared to γ-KetoTCM-1 with a $t_{1/2}$ of 25.9 hours [pseudo $1^{st}$-order rate constant ($k_{obs}$)=(4.52±0.02)×$10^{-5}$ $s^{-1}$, relative rate ($k_{rel.}$)=1.00, and half-life ($t_{1/2}$)=4.26±0.02 h]. The fact that γ-KetoTCM-1 and γ-KetoTCM-2 released COS/$H_2S$ at different rates demonstrates that donor compounds can serve as controllable COS/$H_2S$ donors as COS/$H_2S$ release can be tuned by donor structure modifications. In comparison, γ-KetoTCM-3 and n-BuTCM-1, released negligible PNA in PBS buffer due to the lack of the triggers (e.g., β-H for γ-KetoTCM-3 and γ-keto for n-BuTCM-1), indicating minimum COS/$H_2S$ was released from these two molecules (FIG. 2). Taken together, these structure activity relationship studies demonstrate that donor compounds of the present disclosure are controllable COS/$H_2S$ donors and COS/$H_2S$ release can be achieved through deprotonation/elimination sequence. In addition, COS/$H_2S$ release from donors compounds can be easily visualized and detected due to the simultaneous PNA release, which is a great improvement compared to conventional $H_2S$ donors. UV-Vis characterization and COS/$H_2S$ releasing kinetics are summarized in Table 1.

TABLE 1

UV-Vis characterization and COS/$H_2S$ releasing kinetics of thiocarbamate compounds.

| Donors | $\lambda_{max}$ (nm) | ε ($M^{-1}cm^{-1}$) | pH | $k_{obs}$ (×$10^{-5}$) ($s^{-1}$) | $k_{rel}$ | $t_{1/2}$ (h) |
|---|---|---|---|---|---|---|
| γ-KetoTCM-1 | 333 | 17,600 ± 350 | 6.0 | 0.380 ± 0.006 | 0.0840 | 50.7 ± 0.8 |
| | | | 7.4 | 4.52 ± 0.02 | 1.00 | 4.26 ± 0.02 |
| | | | 7.4[a] | 81.0 ± 3.0 | 18.0 | 0.24 ± 0.01 |
| | | | 8.0 | 12.6 ± 0.2 | 2.79 | 1.53 ± 0.03 |
| γ-KetoTCM-2 | 335 | 14,000 ± 270 | 7.4 | 0.82 ± 0.02 | 0.188 | 23.6 ± 0.7 |
| γ-KetoTCM-3 | 331 | 11,100 ± 220 | 7.4 | N/A | N/A | N/A |
| n-BuTCM-1 | 335 | 13,200 ± 300 | 7.4 | N/A | N/A | N/A |
| γ-KetoCM-1 | 335 | 13,200 ± 300 | 7.4 | 1.44 ± 0.03 | 0.32 | 13.4 ± 0.3 |

[a]PBS contains BSA (5 mg/mL)

γ-KetoTCM-1

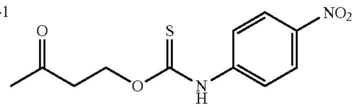

γ-KetoTCM-2

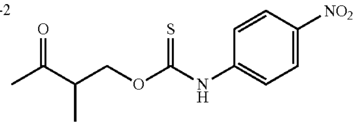

γ-KetoTCM-3

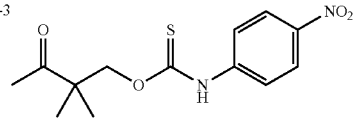

n-buTCM-1

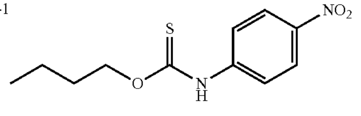

Example 3

In this example, pH effects on COS/$H_2S$ release were investigated by incubating γ-KetoTCM-1 (50 μM) in PBS (pH 6.0-8.0) and monitoring with a UV-Vis spectrometer.

Compared to $COS/H_2S$ release at pH 7.4, pH 8.0 buffer facilitates $COS/H_2S$ release but pH 6.0 buffer results in a much slower and lower $COS/H_2S$ release, which indicates that the rate of PNA formation was significantly enhanced under basic conditions ($k_{rel.}$=2.79 at pH 8.0), indicating a faster $COS/H_2S$ release, whereas PNA formation under acidic conditions was significantly slower ($k_{rel.}$=0.084 at pH 6.0) (Table 1). In particular, a γ-KetoTCM-1 stock solution (15.0 μL, 10.0 mM in DMSO) was added to 3.00 mL of PBS (pH 6.00, 10.0 mM) containing CA (25.0 μg/mL) in a 3-mL UV cuvette. The absorbance (250-500 nm) was measured and recorded at 37° C. $k_{obs}$ was then obtained by plotting the absorbance ratio of PNA and γ-KetoTCM-1 vs time. Since the initial deprotonation reaction was largely inhibited in PBS at pH 6.0, PNA formation from γ-KetoTCM-1 significantly slowed down, indicating a much slower $COS/H_2S$ release under acidic condition.

Figure 3A:
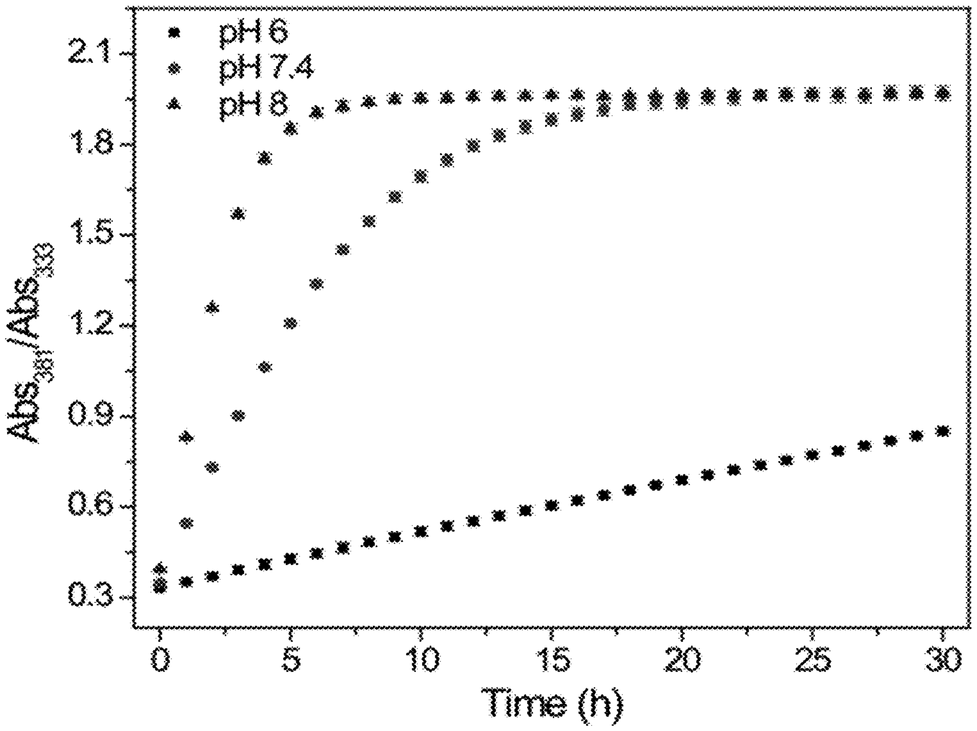
FIG. 3A is a graph showing pH effects on COS/$H_2S$ release from donor compound γ-KetoTCM-1, as monitored by UV.
Figure 3B:
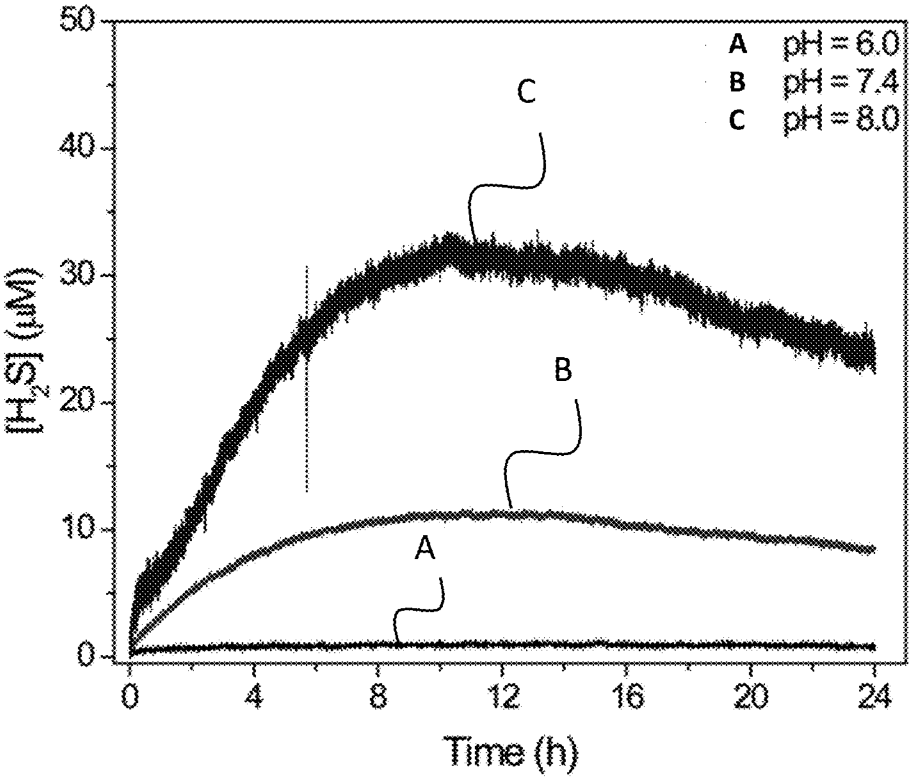
FIG. 3B is a graph showing pH effects on COS/$H_2S$ release from donor compound γ-KetoTCM-1, as monitored by an $H_2S$ electrode.

$H_2S$ release was also observed by using an $H_2S$ electrode, confirming that $H_2S$ was released in this system and such $H_2S$ release was pH-dependent (FIGS. 3A and 3B). This example therefore establishes that $COS/H_2S$ release from compound embodiments of the present disclosure can be pH dependent.

Example 4

Figure 4:
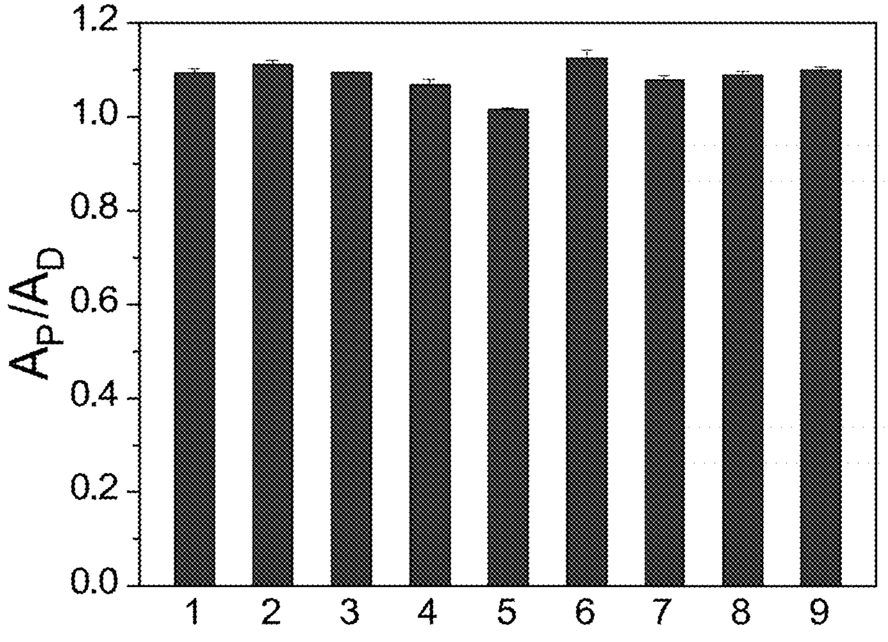
FIG. 4 is a bar graph showing the effects of cellular nucleophiles on COS/$H_2S$ release from donor compound γ-KetoTCM-1, wherein bar 1=phosphate-buffered saline (or "PBS") only; bar 2=cysteine (or "Cys"); bar 3=N-acetyl cysteine (or "NAC"); bar 4=homocysteine (or "Hcy"); bar 5=glutathione (or "GSH"); bar 6=lysine (or "Lys"); bar 7=serine (or "Ser"); bar 8=glycine (or "Gly"); bar 9=glutathione disulfide (or "GSSG") at 5 mM.

To determine the effects of cellular nucleophiles on $COS/H_2S$ release, γ-KetoTCM-1 was incubated in PBS buffer (pH 7.4) was incubated in PBS buffer (pH 7.4, 10 mM) containing (1) no cellular nucleophile (FIG. 4, bar 1); or 250 μM of Cys (FIG. 4, bar 2), 250 μM of N-acetyl cysteine (NAC) (FIG. 4, bar 3), 250 μM of homocysteine (Hcy) (FIG. 4, bar 4), 250 μM of GSH (1.0 mM) (FIG. 4, bar 5), 250 μM of lysine (Lys) (FIG. 4, bar 6), 250 μM of serine (Ser) (FIG. 4, bar 7), 250 μM of glycine (Gly) (FIG. 4, bar 8), or 250 μM of oxidized glutathione (GSSG) (FIG. 4, bar 9) at 37° C. PNA formation was monitored and recorded after a 4-hour incubation using UV-vis spectroscopy. None of the tested nucleophiles resulted in substantial PNA formation by comparison to the background reaction, demonstrating that $COS/H_2S$ release from γ-KetoTCM-1 is solely pH-dependent and not facilitated directly by common cellular nucleophiles.

Example 5

In this example, compound activation and subsequent $COS/H_2S$ release in PBS containing bovine serum albumin (BSA) was evaluated to mimic a complex biological environment. γ-KetoTCM-1 (50 μM) was incubated in PBS (pH 7.4, 10 mM) containing BSA (5 mg/mL) and CA (25 μg/mL) at 37° C. In particular, A γ-KetoTCM-1 stock solution (15.0 μL, 10.0 mM in DMSO) was added to 3.00 mL of PBS (pH 7.40, 10.0 mM) containing BSA (5.00 mg/mL) and CA (25.0 μg/mL) in a quartz UV cuvette. The absorbance (250-500 nm) was measured and recorded by using an Agilent Cary 100 UV-Vis spectrometer at 37° C.

Figure 5A:
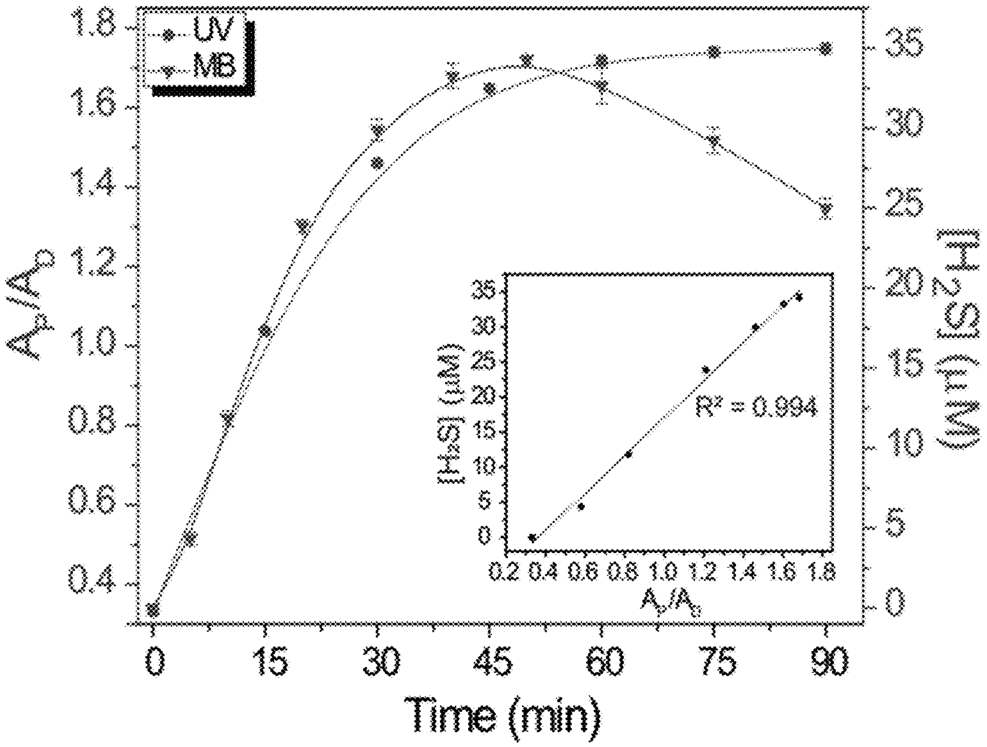
FIG. 5A is a graph showing PNA formation (curve labeled with a "●" symbol) and $H_2S$ release (curve labled with a "▼" symbol) upon γ-KetoTCM-1 (50 μM) activation in PBS (pH 7.4, 10 mM) containing BSA (5 mg/mL) at 37° C. and wherein the insert shows the correlation between measured [$H_2S$] and PNA formation.
Figure 5B:
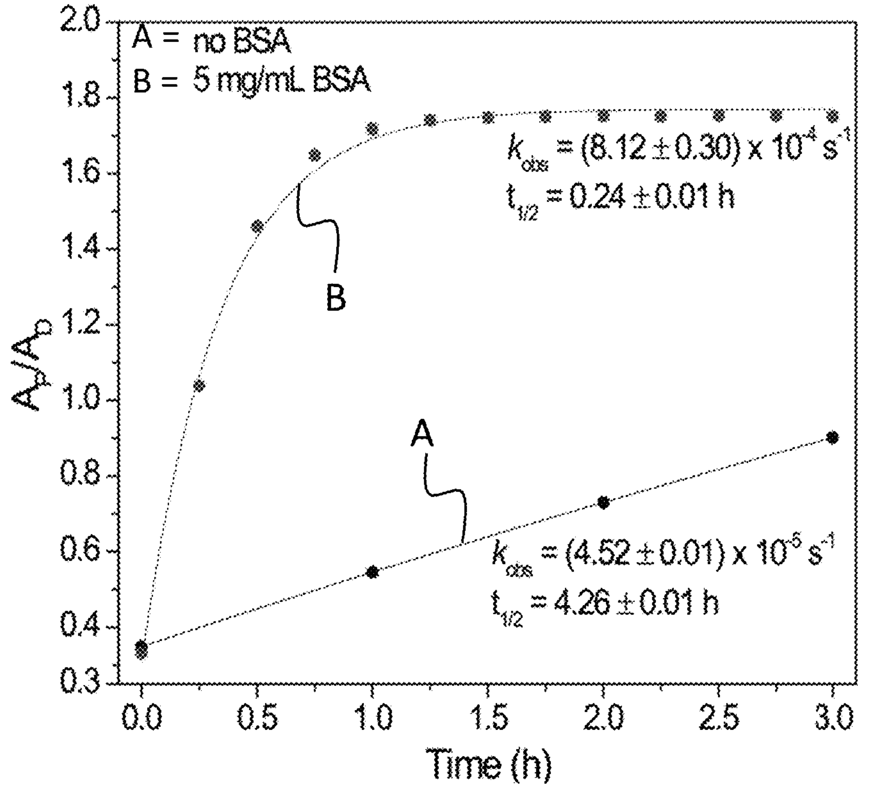
FIG. 5B is a graph showing BSA-catalyzed PNA formation from γ-KetoTCM-1.

Under these conditions, a significantly faster activation of γ-KetoTCM-1 ($k_{rel.}$=18.0) was observed (FIG. 5A, curve labeled with "●" symbol; and FIG. 5B). These results indicate that the $COS/H_2S$ releasing kinetics of γ-KetoTCM-1 may be faster under biological conditions than that in simple aqueous buffers, but also highlights the benefit of a colorimetric response upon donor activation.

Figure 6:
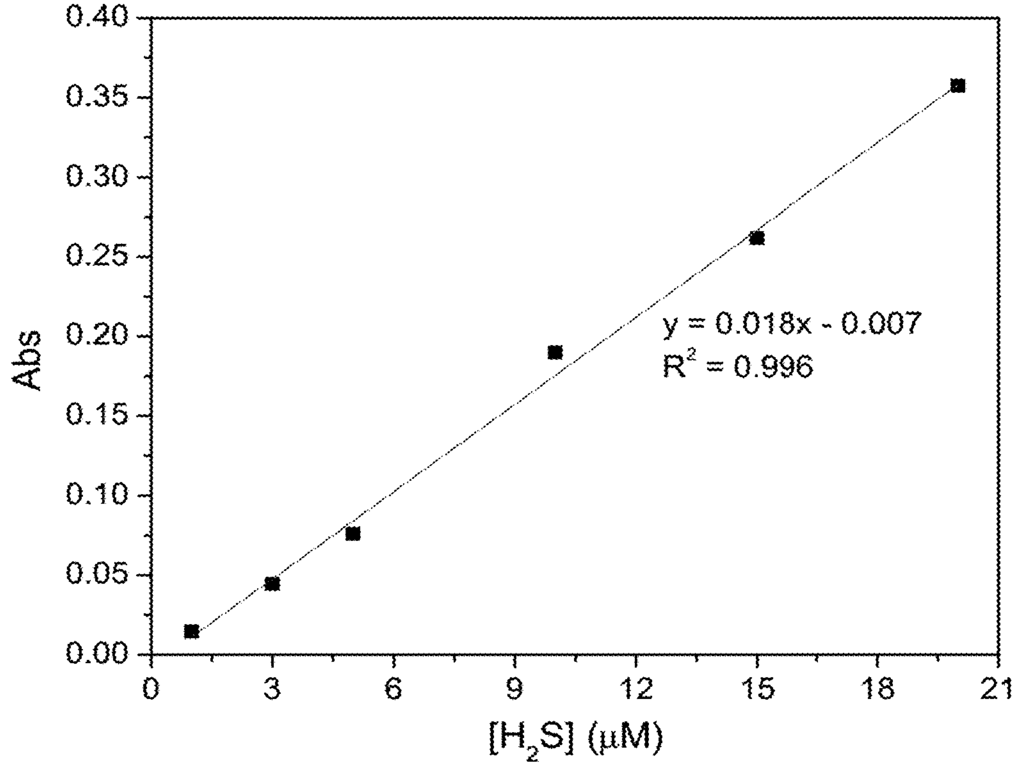
FIG. 6 is an $H_2S$ calibration curve generated using a method described herein.

Using the same conditions, $H_2S$ production was measured at different time points using the MB assay (FIG. 5A, curve labeled with the "▼" symbol). The MB assay allows for $H_2S$ quantification from the reaction of $H_2S$ with N,N-dimethyl-p-phenylenediamine in the presence of $FeCl_3$ and acid to produce methylene blue (MB, $\lambda_{max}$=670). In the MB assay, a γ-KetoTCM-1 stock solution (100 μL, 10.0 mM in DMSO) was added to 20.0 mL of PBS (pH 7.40, 10.0 mM) containing BSA (5.00 mg/mL) and CA (25.0 μg/mL) in a 25-mL scintillation vial at 37° C. Next, 0.300 mL aliquots of the reaction mixture were transferred to UV cuvettes containing 0.300 mL of MB cocktail at different time points. The MB reaction mixture was incubated at room temperature for 1 hour and the precipitate was removed using syringe filters. The absorbance at 670 nm was then measured and was converted to $H_2S$ concentration by using the $H_2S$ calibration curve in FIG. 6. The calibration curve was generated as follows: to 1.50 mL-UV cuvettes were added 500 μL of MB cocktail (60.0 μL $Zn(OAc)_2$ (1.00% w/v), 120 μL $FeCl_3$ (30.0 mM in 1.20 M HCl) and 120 μL N,N-dimethyl-p-phenylene diamine (20.0 mM in 7.20 M HCl)) and 500 μL PBS buffer (pH 7.40, 10.0 mM). The resultant solution was mixed thoroughly, followed by the addition of an NaSH stock solution (1.00 mM) to make the final $H_2S$ concentrations of 1.00, 3.00, 5.00, 10.0, 15.0, and 20.0 μM. The MB solution was allowed to react with $H_2S$ for 1 hour before measuring the absorbance at 670 nm.

Figure 7:
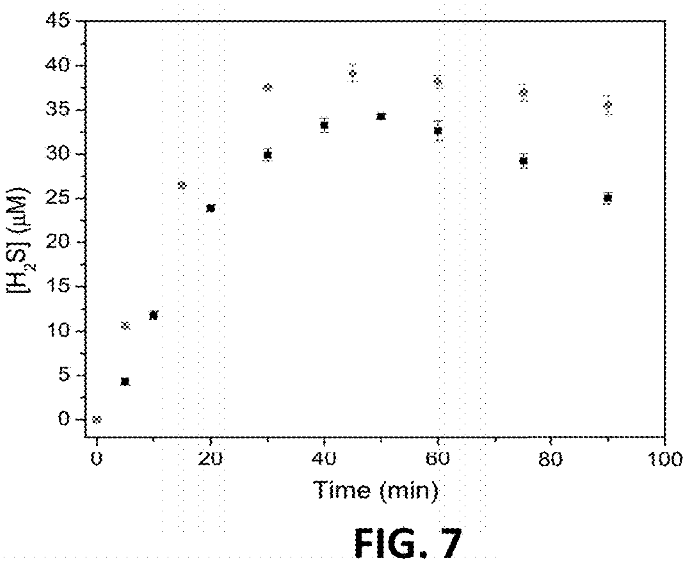
FIG. 7 is a graph showing $H_2S$ Release from γ-KetoTCM-1 with (curve labeled with a "●" symbol) or without (curve labeled with a "■" symbol) argon protection.

A linear relationship (first 60 minutes) was obtained by plotting the absorbance ratio of PNA and γ-KetoTCM-1 vs $H_2S$ concentrations measured by MB assay, indicating that PNA can serve as a reliable optical tool to monitor $COS/H_2S$ release from γ-KetoTCM-1. The linearity between these two methods was lost after 60 minutes due to the oxidation of $H_2S$ in the MB assay at extended incubation times (FIG. 5A). Using this assay, a 70% $H_2S$ release efficiency was observed. This is attributed to the slight decrease in $H_2S$ at extended time points to aerobic $H_2S$ oxidation (FIG. 7). In this example, the experiments were repeated with argon (Ar) protection. In particular, a γ-KetoTCM-1 stock solution (100 μL, 10.0 mM in DMSO) was added to 20.0 mL of degassed PBS (pH 7.40, 10.0 mM) containing BSA (5.00 mg/mL) and CA (25.0 μg/mL) in a 20-mL scintillation vial at 37° C. under Ar. Next, 0.300 mL aliquots of the reaction mixture were transferred to UV cuvettes containing 0.300 mL of MB cocktail at different time points. The MB reaction mixture was incubated at room temperature for 1 hour and the precipitate was removed using syringe filters. The absorbance at 670 nm was then measured and converted to $H_2S$ concentration by using the $H_2S$ calibration curve in FIG. 6. Although a slight decrease in $H_2S$ was still observed, the overall $H_2S$ release under the Ar protection maintained an elevated state at extended time points (FIG. 7, curve labelled with "●" symbol) by comparison to the aerobic measurements (FIG. 7, curve labelled with "■" symbol), which is consistent with less oxidation under Ar-protected conditions.

Figure 8A:
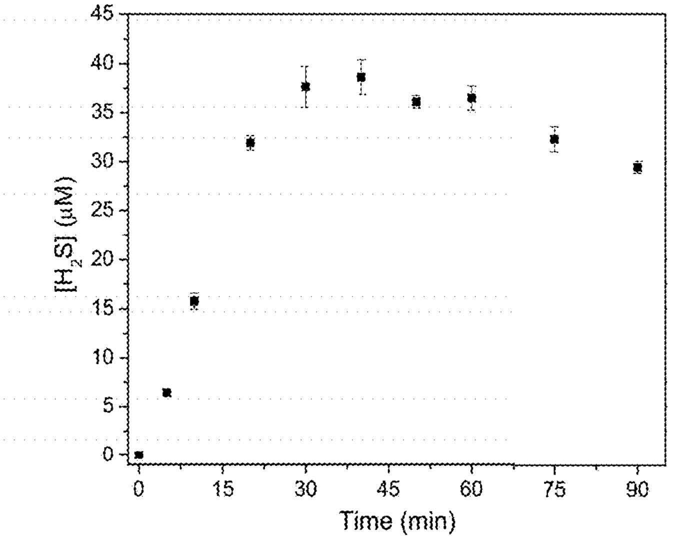
FIG. 8A is a graph showing $H_2S$ release from γ-KetoTCM-1 in the presence of PNA.
Figure 8B:
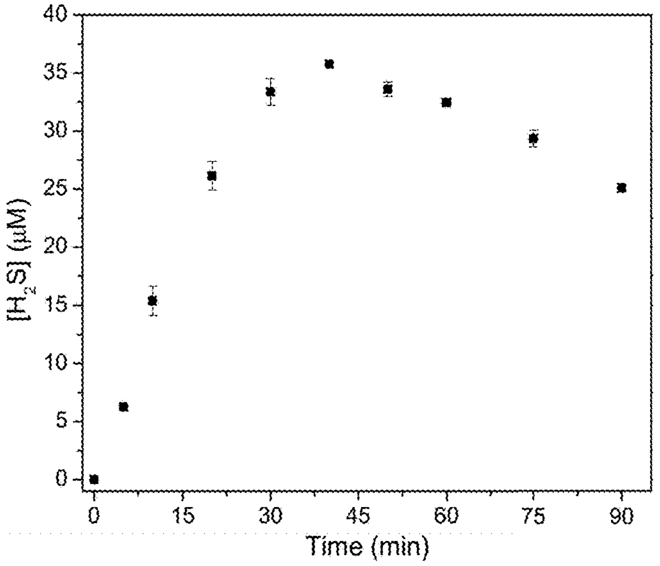
FIG. 8B is a graph showing $H_2S$ release from γ-KetoTCM-1 in the presence of methyl vinyl ketone (MVK).

It was confirmed that the reaction by-products, PNA and methy vinyl ketone (MVK), did not provide a positive response on their own, nor did they react further with $H_2S$ (FIGS. 8A and 8B). In particular, a γ-KetoTCM-1 stock solution (100 μL, 10.0 mM in DMSO) was added to 20.0 mL of PBS (pH 7.40, 10.0 mM) containing PNA or MVK (50 μM), BSA (5.00 mg/mL) and CA (25.0 μg/mL) in a 25-mL scintillation vial at 37° C. Next, 0.300 mL aliquots of the reaction mixture were transferred to UV cuvettes containing 0.300 mL of MB cocktail at different time points. The MB reaction mixture was incubated at room temperature for 1 hour and the precipitate was removed using syringe filters. The absorbance at 670 nm was then measured and was converted to $H_2S$ concentration by using the $H_2S$ calibration curve in FIG. 6.

Fitting the MB data up to the plateau point (~60 minutes) afforded a peudo first-order rate constant of $k_{obs.}=(8.6\pm0.9)\times10^{-4}$ $s^{-s}$, which matches the $(8.1\pm0.3)\times10^{-4}$ $s^{-1}$ value obtained from fitting the UV-vis data, thus confirming that the UV-vis signal correlates directly with $H_2S$ release. In addition, the strong correlation between these two methods suggests that PNA can serve as a reliable optical tool to profile the $COS/H_2S$ releasing capacities of γ-KetoTCM donors (FIG. 5A, insert).

Example 6

Figure 9:
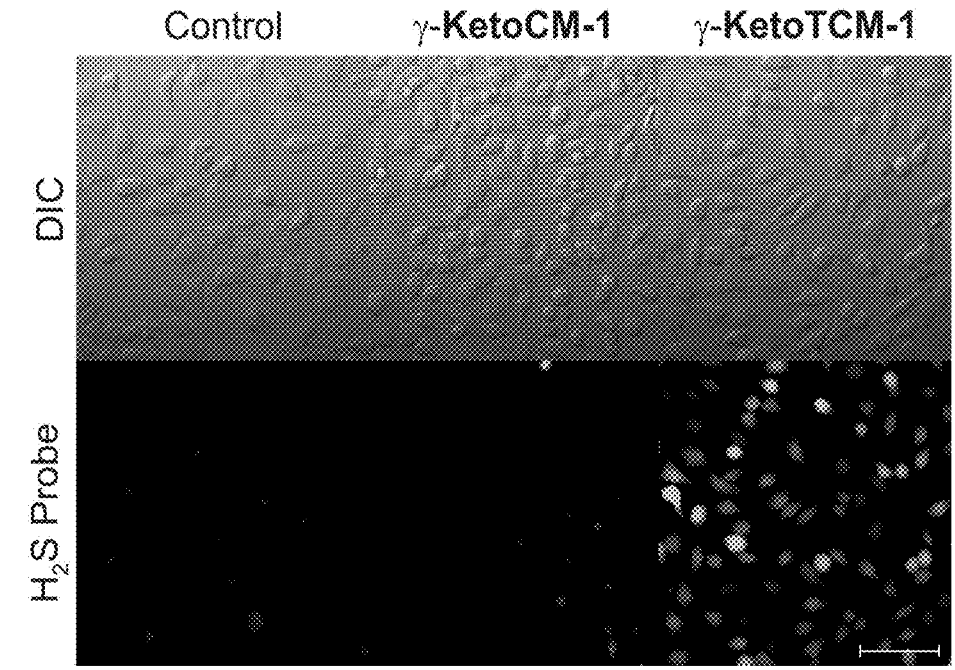
FIG. 9 provides images of $H_2S$ Delivery from γ-KetoTCM-1 in HeLa cells, wherein the HeLa cells were treated with SF7-AM (5 μM) for 30 minutes, washed, and incubated with FBS-free DMEM only (left top and bottom images), with 100 μM γ-KetoCM-1 (middle top and bottom images), or with γ-KetoTCM-1 (right top and bottom images) for 2 hours.

In this example, it was evaluated whether γ-KetoTCM-based donors can be activated to deliver $H_2S$ in cellular environments. SF7-AM, a cell-trappable $H_2S$ fluorescent probe, was used to monitor $H_2S$ accumulation from γ-KetoTCM-1 in HeLa cells. In the absence of γ-KetoTCM-1, no fluorescent signal from SF7-AM was observed, indicating negligible endogenous $H_2S$ (FIG. 9, left column, including the top and bottom images). Treating cells with carbamate control γ-KetoCM-1 also failed to provide a SF7-AM signal, suggesting that the MVK and PNA by-products did not provide a false-positive or upregulate $H_2S$ generation pathways (FIG. 9, middle column, including the top and bottom images). By contrast, addition of γ-KetoTCM-1 resulted in a significant increase in SF7-AM fluorescence, demonstrating that γ-KetoTCM-1 can be successfully activated in a cellular environment and that the released $H_2S$ can be visualized using an $H_2S$-responsive fluorescent probe (FIG. 9, right column, including the top and bottom images).

HeLa cells were cultured in high glucose Dulbecco's modified Eagle's medium (DMEM) supplemented with 10% fetal bovine serum (FBS) and 1% penicillin/streptomycin at 37° C. under 5% $CO_2$. Confluent RAW 264.7 cells were incubated in FBS-free DMEM containing vehicle (0.5% DMSO), γ-KetoTCM-1, γ-KetoTCM-3, γ-KetoCM-1, and n-BuTCM-1 (10.0-100 μM) for 6 hours in a 96-well plate. The culture media were then removed and 100 μL of FBS-free DMEM containing 10% CCK-8 solution was added to each well, and cells were incubated for 2 hours at 37° C. The absorbance at 450 nm was measured by using a micropate reader. The cell viability was measured and normalized to the vehicle group. The results are expressed as mean±SEM (n=6).

HeLa cells were plated in poly-D-lysine coated plates (MatTek) containing 2.00 mL of DMEM and incubated at 37° C. under 5% $CO_2$ for 24 hours. The confluent cells were washed with PBS and then co-incubated with SF7-AM (5.00 μM) and NucBlue nuclear dye (2 drops) for 30 minutes. The cells were then washed with PBS and incubated with either γ-KetoTCM-1 (100 μM) or γ-KetoCM-1 (100 μM) alone for 2 hours. Prior to imaging, the cells were washed with PBS and bathed in 2.00 mL of PBS. Cell imaging was performed on a Leica DMi8 fluorescent microscope.

Example 7

In this example, the ability of embodiments of the disclosed donor compound to provide anti-inflammatory activity was evaluated. To investigate the potential protective effects of the developed donors, pretreated macrophage RAW 264.7 cells were pretreated with γ-KetoTCM-1 (25 μM) for 6 hours, followed by an 18-hour incubation with lipopolysaccharide (LPS, 1.0 μg/mL) to induce an inflammatory response. This response is accompanied by an increase in NO production, which was monitored by measuring nitrite ($NO_2^-$) accumulation. To determine whether the observed effects were due to $COS/H_2S$ release, control experiments with γ-KetoTCM-3, γ-KetoCM-1, and GYY4137 under the identical condition also were performed.

Figure 10:
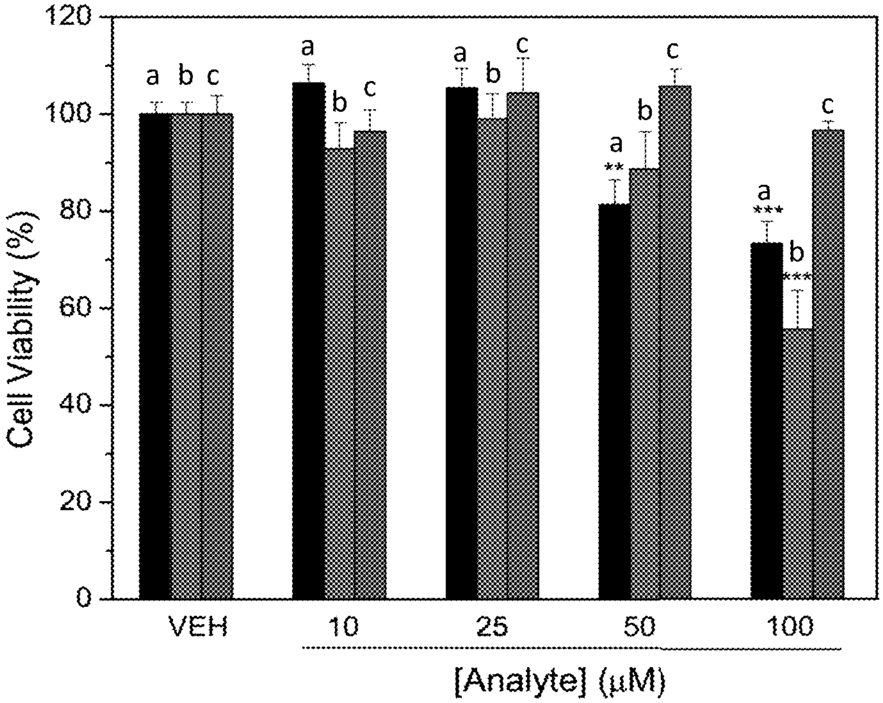
FIG. 10 is a graph showing that COS/$H_2S$ releasing rate at pH 7.4 is moderate with a half-life time ($t_{1/2}$) of 4.26 hours at 37° C.

GYY4137 was used as a positive control because it has shown anti-inflammatory effects previously, and because it generates a slow, continuous release of $H_2S$. 25 μM of each compound in this study because this concentration did not provide significant cytotoxicity (FIG. 10).

Figure 11:
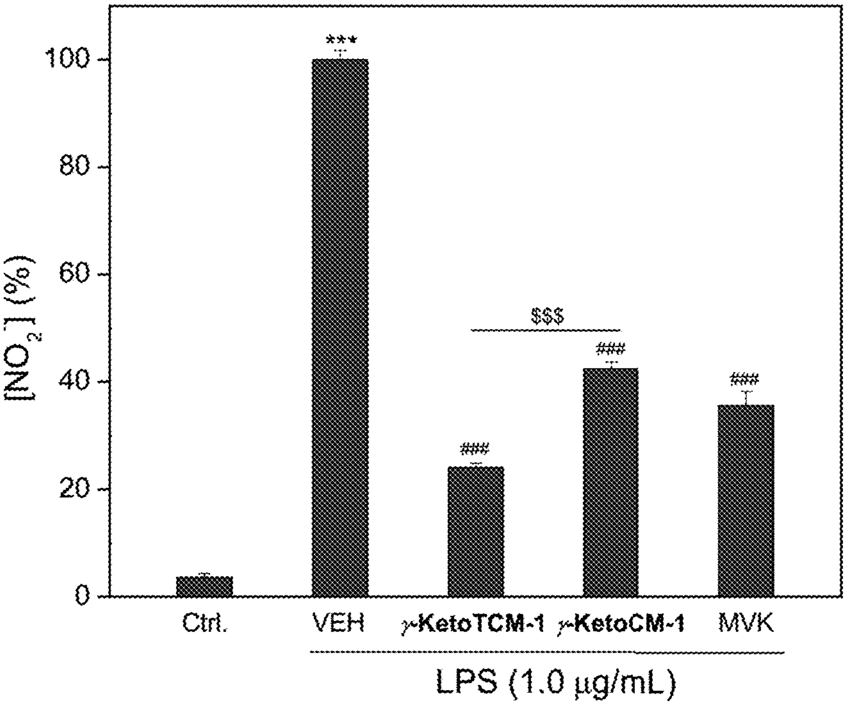
FIG. 11 is a bar graph showing results from evaluating the effects of MVK against LPS-induced inflammation, wherein the results are expressed as mean±SD (n=4) and ***=P<0.001 vs the control group; ###=P<0.001 vs vehicle-treated group; and $^{\$\$\$}$=P<0.001 between γ-KetoTCM-1-treated and γ-KetoCM-1-treated groups.
Figure 12:
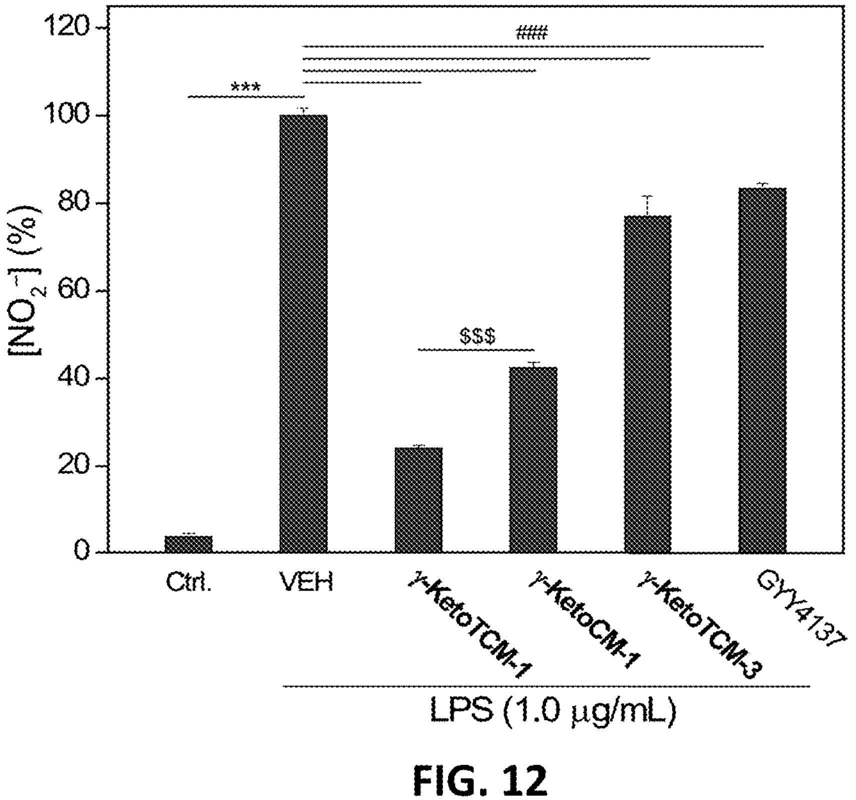
FIG. 12 is a bar graph showing results from evaluating Effects of γ-KetoTCM-1 on LPS-induced $NO_2^-$ formation, wherein results are expressed as mean±SD (n=4) and ***=P<0.001 vs the control group; $^{\#\#\#}$=P<0.001 vs vehicle-treated group; and $^{\$\$\$}$=P<0.001 between γ-KetoTCM-1-treated and γ-KetoCM-1-treated groups.

In comparison to the control group, in which cells were only incubated in FBS-free DMEM, the LPS-treated cells showed a significant $NO_2^-$ increase. γ-KetoTCM-1 pretreatment, however, significantly reduced LPS-induced $NO_2^-$ production. Control experiments using γ-KetoCM-1 also reduced $NO_2^-$ levels, although to a lesser extent than γ-KetoTCM-1. The results from KetoCM-1 may be attributed to MVK release, which was confirmed independently (FIG. 11). A modest reduction of LPS-induced $NO_2^-$ production also was observed from γ-KetoTCM-3, although this effect was significantly attenuated from that of γ-KetoTCM-1. GYY4137 exhibited a less pronounced effect on LPS-induced $NO_2^-$ production at the same concentration (25 μM), which supports the increased efficiency of γ-KetoTCM-1 (FIG. 12). Taken together, these data demonstrate that γ-KetoTCM-1 can deliver $H_2S$ in complex environment and provide protection against LPS-induced inflammation, suggesting potential therapeutic applications of γ-KetoTCM-based $H_2S$ donors. In addition these experiments highlight the benefits of having access to key control compounds that enable specific contributions to cellular protections to be analysed.

In this example, macrophage RAW 264.7 cells were seeded in a 24-well plate ($5\times10^5$ cells/well) containing 0.50 mL of DMEM and incubated at 37° C. under 5% $CO_2$ for 24 hours. The confluent cells were washed with PBS and incubated with either γ-KetoTCM-1, γ-KetoTCM-3, γ-KetoCM-1, or GYY4137 (25.0 μM) at 37° C. for 6 hours. Compounds were then removed by washing cells with PBS and these pretreated cells were incubated in FBS-free DMEM containing LPS (1.00 μg/mL) for 18 hours. $NO_2^-$ levels were measured by using a Griess Reagent Kit.

Since γ-KetoCM-1 exhibited anti-inflammatory activity, an investigation as to whether such protection was due to γ-KetoCM-1 itself or the by-product, such as MVK, upon compound activation was conducted. A similar anti-inflammatory protection was observed when incubating RAW 264.7 cells with authentic MVK (25.0 μM), indicating that the observed protective activity of γ-KetoCM-1 was due to MVK release.

Example 8

In this example, a donor compound is administered to a subject by preparing a pharmaceutical composition comprising the donor compound and a pharmaceutically acceptable excipient. The composition is administered either by administering an oral dosage form comprising the composition to the subject, by injecting the composition at a site of interest, by intraperitoneal injection, or by applying a topical ointment comprising the composition at a site of interest. The subject is then optionally administered a separate pharmaceutical composition comprising a conversion component. The subject is evaluated for an increase in concentration of $H_2S$ by taking a blood sample from the subject and determining the concentration of $H_2S$ in the blood sample as compared to a blood sample taken from the subject prior to administration of the pharmaceutical composition comprising the donor compound.

Example 9

In this example, a donor compound is administered to a sample by exposing the sample to a composition comprising the donor compound. The sample is then optionally exposed to a separate composition comprising a conversion component. The sample is evaluated to determine if a detectable signal is emitted within the sample after exposure to the composition comprising the donor compound. The evaluation step can comprise analyzing the sample using a spectrofluorometer, a fluorescent microscope, a fluorescence scanner, or a flow cytometer.

In view of the many possible embodiments to which the principles of the present disclosure may be applied, it should be recognized that the illustrated embodiments are only preferred examples and should not be taken as limiting the scope of the present disclosure. Rather, the scope is defined by the following claims. We therefore claim as our invention all that comes within the scope and spirit of these claims.

We claim:

1. A compound represented by Formula I

Formula 1

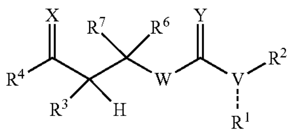

wherein

X is oxygen, sulfur, NR' or $N^+(R')_2$, wherein each R' independently is hydrogen, aliphatic, haloaliphatic, haloheteroaliphatic, heteroaliphatic, aromatic, or any combination thereof;

W is oxygen or sulfur;

when Y is oxygen then W is sulfur; or when Y is sulfur then W is oxygen or sulfur;

V is a heteroatom;

$R^1$, if present, is hydrogen, aliphatic, haloaliphatic, haloheteroaliphatic, heteroaliphatic, aromatic, or any combination thereof;

if V is nitrogen, then $R^2$ is aliphatic, aromatic, or $R^1$ and $R^2$ when taken together with V is a heteroaliphatic group, provided that if $R^2$ is aliphatic, then the aliphatic group is not substituted with a =O group;

$R^2$ is aliphatic, aromatic, heteroaliphatic, or $R^1$ and $R^2$ when taken together with V is a heteroaliphatic group;

$R^3$ is hydrogen or aliphatic;

$R^4$ is aliphatic; and each of $R^6$ and $R^7$ independently is hydrogen.

2. The compound of claim 1, wherein $R^2$ is aromatic; -aromatic-$(R^5)_m$, wherein m is an integer selected from 0-5 and each $R^5$ independently is $NO_2$, $NH_2$, or OMe.

3. The compound of claim 1, wherein X is oxygen, sulfur, or NR' or $N^+(R')_2$, wherein each R' independently is hydrogen, alkyl, akenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-arylalkenyl-arylalkynyl-aryl, alkyl-heteroaryl/alkenyl-heteroarylalkynyl-heteroaryl, heteroalkyl-arylheteroalkenyl-arylheteroalkynyl-aryl, heteroalkyl-heteroarylheteroalkenyl-heteroaryl/heteroalkynyl-heteroarylor any combination thereof; and wherein V is oxygen, sulfur, or nitrogen.

4. The compound of claim 1, wherein $R^1$ is present and is hydrogen, alkyl, alkenyl, alkynyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-arylalkenyl-arylalkynyl-aryl, alkyl-heteroarylalkenyl-heteroarylalkynyl-heteroaryl, heteroalkyl-aryl/heteroalkenyl-aryl/heteroalkynyl-aryl, heteroalkyl-heteroarylheteroalkenyl-heteroaryheteroalkynyl-heteroaryl, or any combination thereof.

5. The compound of claim 1, wherein $R^3$ is hydrogen; alkyl; alkenyl; alkynyl; or any combination thereof.

6. The compound claim 1, wherein $R^4$ is alkyl, alkenyl alkynyl, or any combination thereof.

7. The compound of claim 1, wherein $R^2$ is aryl; heteroaryl; -aliphatic-aryl; -aliphatic-heteroaryl; -heteroaliphatic-aryl; heteroalkyl-heteroaryl; heteroalkenyl-heteroaryl; heteroalkynyl-heteroaryl; or -aliphatic-aryl-$(R^5)_m$, -aliphatic-heteroaryl-$(R^5)_m$, -heteroaliphatic-aryl-$(R^5)_m$, heteroalkyl-heteroaryl-$(R^5)_m$, heteroalkenyl-heteroaryl-$(R^5)_m$, heteroalkynyl-heteroaryl-$(R^5)_m$, -aryl-$(R^5)_m$ or -heteroaryl-$(R^5)_m$ wherein m is an integer selected from 0-5 and each $R^5$ independently is nitro, amine, or methoxy; $R^3$ is hydrogen or lower alkyl; $R^4$ is lower alkyl.

8. The compound of claim 1, wherein $R^2$ comprises 4-methyl-2H-chromen-2-one, 2-(2-methoxyethyl)-1H-benzo[de]isoquinoline-1,3(2H)-dione, or methylrhodol.

9. The compound of claim 1, wherein the compound is represented by any one of Formulas 2A-2I:

Formula 2A

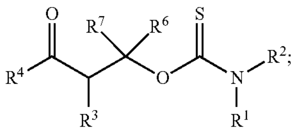

Formula 2B

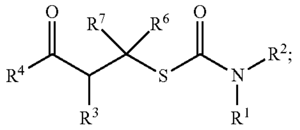

Formula 2C

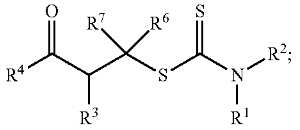

Formula 2D

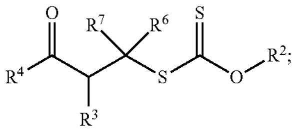

Formula 2E

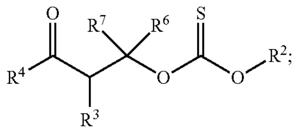

Formula 2F

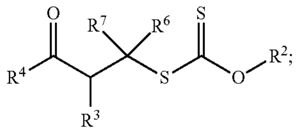

-continued

Formula 2G

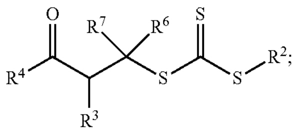

Formula 2H

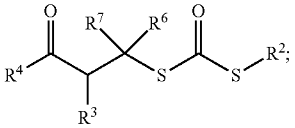

or

Formula 2I

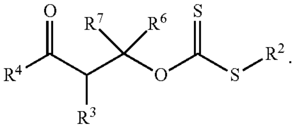

10. The compound of claim 1, wherein the compound is represented by an one of Formulas 3A-3I:

Formula 3A

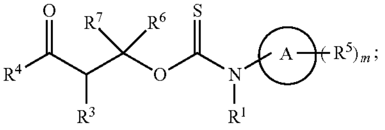

Formula 3B

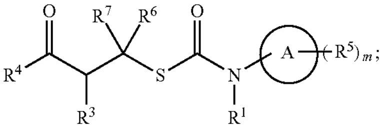

Formula 3C

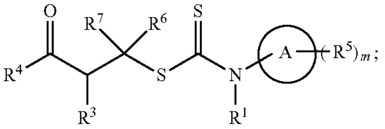

Formula 3D

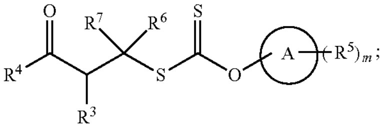

Formula 3E

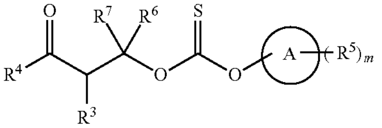

Formula 3F

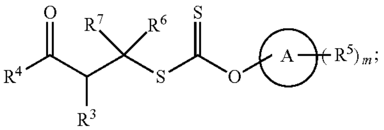

Formula 3G

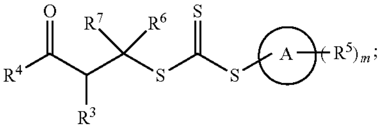

-continued

Formula 3H

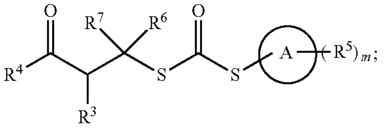

or

Formula 3I

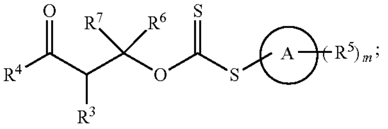

wherein m is an integer selected from 0-5 and each $R^5$ independently is $NO_2$, $NH_2$, or OMe; and ring A is an aromatic group, an aliphatic-aryl group, an aliphatic-heteroaryl group, a heteroaliphatic-aryl group, a heteroalkyl-heteroaryl group, a heteroalkenyl-heteroaryl group, or a heteroalkynyl-heteroaryl group.

11. A compound selected from:

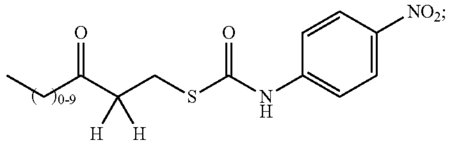

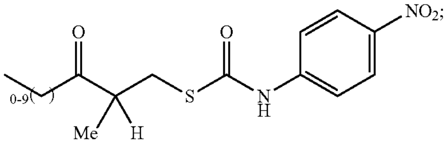

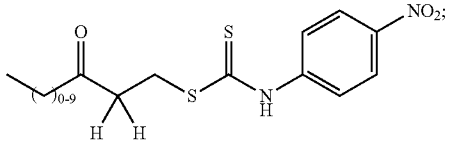

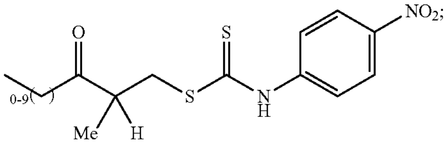

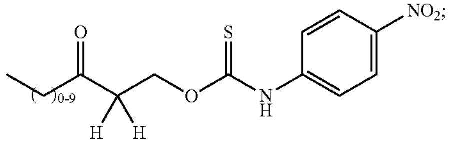

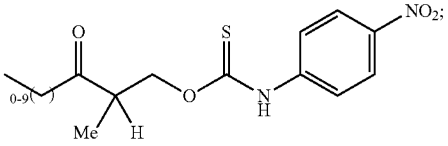

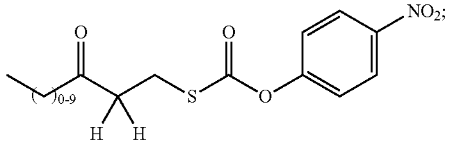

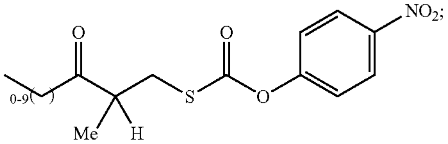

-continued
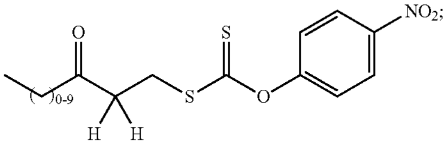
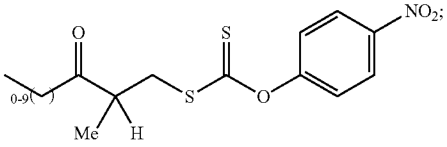
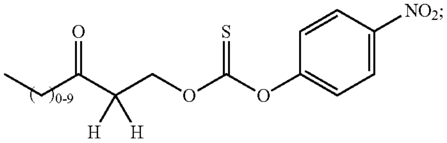
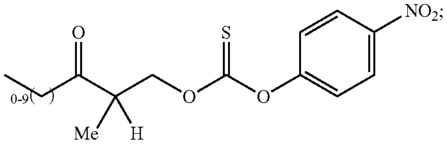
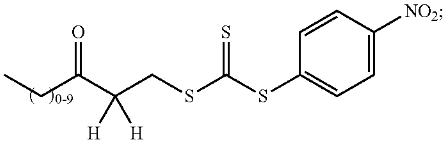
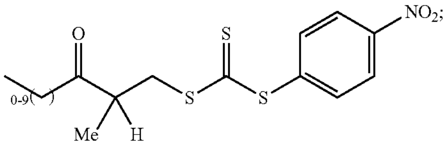
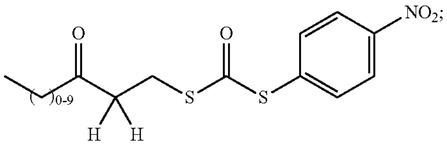
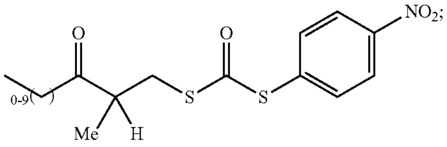
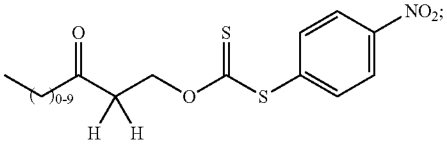
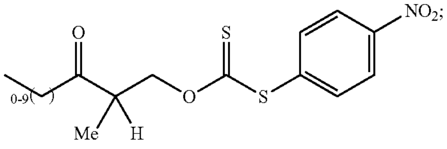
-continued
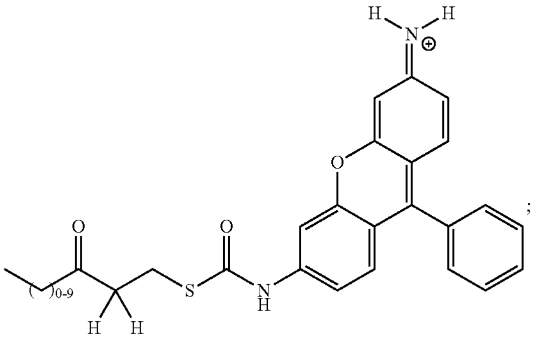
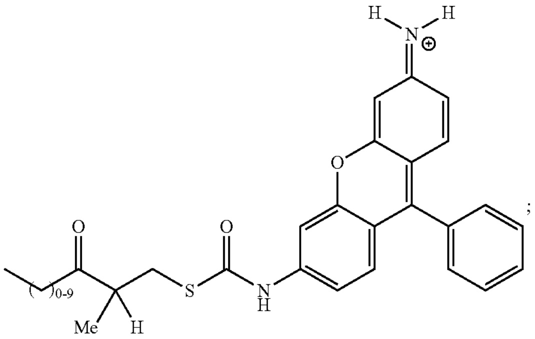
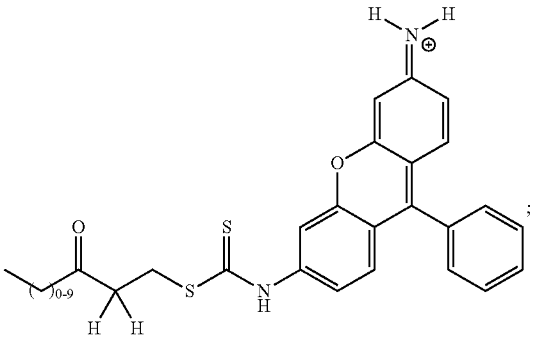
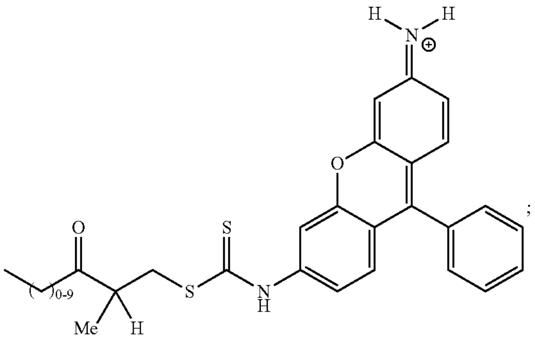
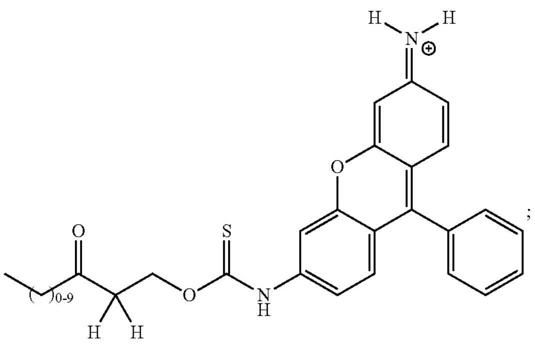

-continued
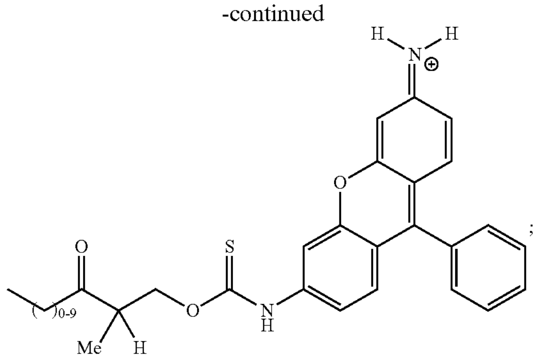
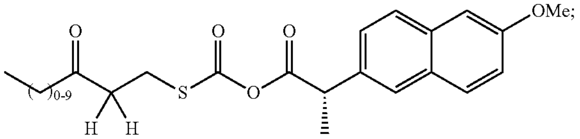
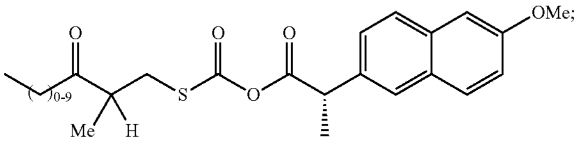
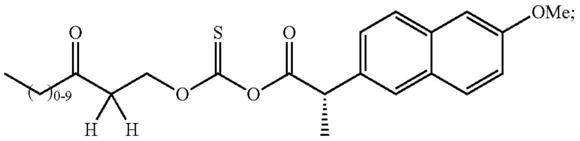
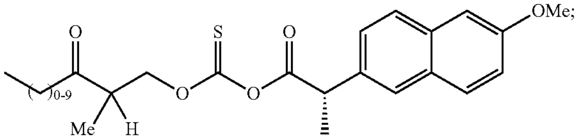
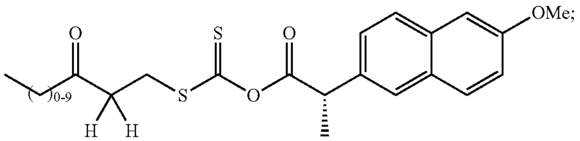
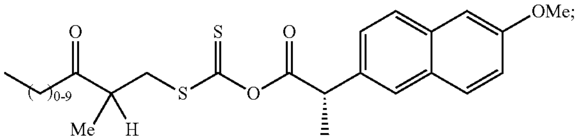
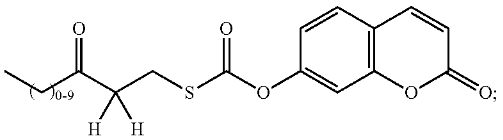
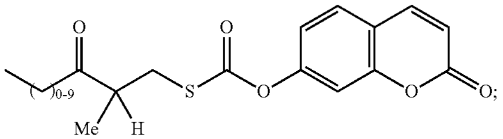
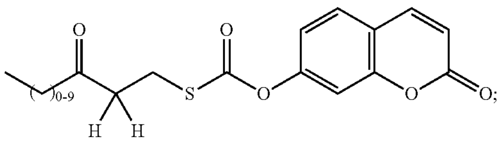
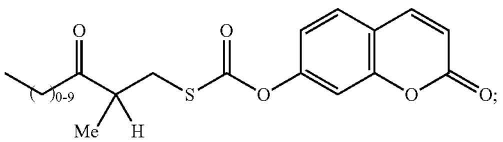
-continued
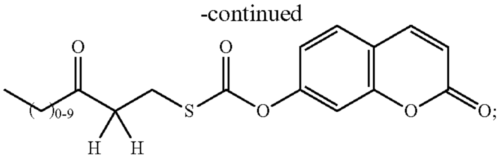
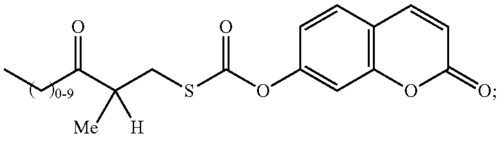
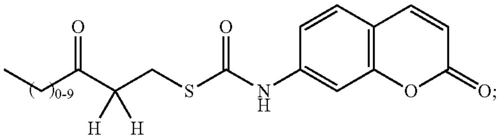
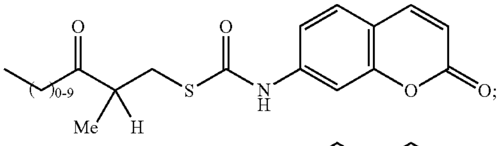
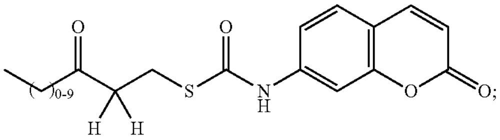
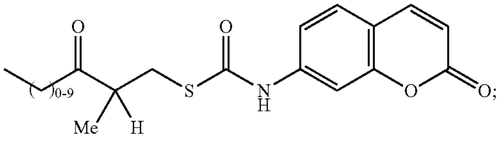
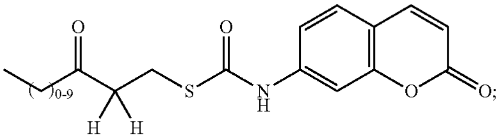
or
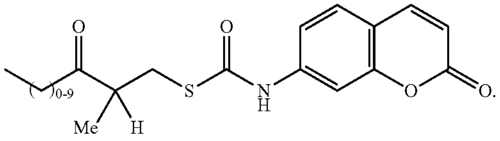
12. A compound selected from:
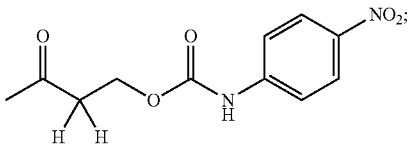
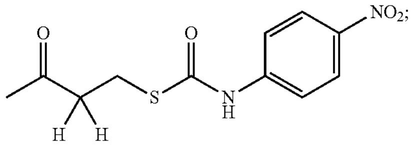
or
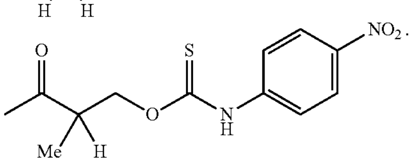
13. A pharmaceutical composition, comprising a compound according to claim 1, and an additional compositional component selected from a pharmaceutically acceptable excipient, water, a buffer, a conversion component, or two or more thereof.

14. The compound of claim 1, wherein $R^2$ and $R^1$ together with V form a 4-, 5-, 6-, or 7-membered heterocyclic group.

* * * * *